US 8,784,668 B2

(12) United States Patent
Beiriger

(10) Patent No.: US 8,784,668 B2
(45) Date of Patent: Jul. 22, 2014

(54) SYSTEMS AND METHODS FOR COMPENSATION OF COMPLIANT BEHAVIOR IN REGENERATIVE DIALYSIS SYSTEMS

(75) Inventor: Michael J Beiriger, Pittsburgh, PA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 286 days.

(21) Appl. No.: 12/902,702

(22) Filed: Oct. 12, 2010

(65) Prior Publication Data

US 2012/0085707 A1  Apr. 12, 2012

(51) Int. Cl.

| B01D 61/22 | (2006.01) |
|---|---|
| B01D 61/14 | (2006.01) |
| B01D 61/18 | (2006.01) |
| B01D 61/32 | (2006.01) |
| B01D 61/26 | (2006.01) |
| B01D 61/28 | (2006.01) |
| B01D 61/30 | (2006.01) |
| B01D 61/24 | (2006.01) |
| A61M 1/16 | (2006.01) |

(52) U.S. Cl.
CPC ...... *B01D 61/243* (2013.01); *A61M 2205/3393* (2013.01); *B01D 2311/2626* (2013.01); *B01D 61/30* (2013.01); *B01D 2311/16* (2013.01); *A61M 1/1696* (2013.01); *B01D 61/32* (2013.01)
USPC ............ 210/744; 210/85; 210/86; 210/97; 210/103; 210/104; 210/109; 210/134; 210/143; 210/252; 210/257.1; 210/257.2; 210/258; 210/321.6; 210/321.65; 210/645; 210/646; 210/650; 210/660; 210/739

(58) Field of Classification Search
CPC ............... A61M 1/1696; A61M 2205/3393; B01D 2311/16; B01D 2311/2626; B01D 61/243; B01D 61/30; B01D 61/32

USPC ............ 210/645, 646, 660, 739, 844, 85, 86, 210/97, 103, 104, 109, 134, 143, 252, 210/257.1, 257.2, 258, 321.6, 321.65, 650
See application file for complete search history.

(56) References Cited

U.S. PATENT DOCUMENTS

| 3,871,913 A | 3/1975 | Shaldon |
|---|---|---|
| 4,174,231 A | 11/1979 | Hobgood |

(Continued)

FOREIGN PATENT DOCUMENTS

| EP | 0278100 | 8/1988 |
|---|---|---|
| EP | 0673658 | 9/1995 |

(Continued)

OTHER PUBLICATIONS

"RX Guide to Custom Dialysis," COBE Renal Care Inc., Revision E. Sep. 1993.

(Continued)

*Primary Examiner* — John Kim
(74) *Attorney, Agent, or Firm* — Onello & Mello, LLP

(57) ABSTRACT

In a regenerative dialysis system, in a method for controlling a regenerative dialysis system, and in a controller for a regenerative dialysis system, an embodiment of the system comprises an input pump that pumps fresh dialysate fluid into a dialyzer at an input rate. An output pump pumps used dialysate fluid from the dialyzer at an output rate. An ultrafiltration rate of the system is related to the output rate relative to the input rate. A sorbent cartridge filters the used dialysate fluid to generate the fresh dialysate fluid. A controller controls the ultrafiltration rate of the system in response to a flow rate of the dialysate fluid through the sorbent cartridge.

20 Claims, 9 Drawing Sheets

(56) References Cited

U.S. PATENT DOCUMENTS

| | | | |
|---|---|---|---|
| 4,191,351 A | 3/1980 | Goyne | |
| 4,581,141 A | 4/1986 | Ash | |
| 4,661,246 A * | 4/1987 | Ash | 210/87 |
| 4,666,598 A | 5/1987 | Heath et al. | |
| 4,684,460 A | 8/1987 | Issautier | |
| 4,728,496 A | 3/1988 | Petersen et al. | |
| 4,770,787 A | 9/1988 | Heath et al. | |
| 4,784,495 A | 11/1988 | Jonsson et al. | |
| 4,789,467 A | 12/1988 | Lindsay et al. | |
| 4,997,577 A | 3/1991 | Stewart | |
| 5,256,371 A | 10/1993 | Pippert | |
| 5,262,068 A | 11/1993 | Bowers et al. | |
| 5,277,820 A | 1/1994 | Ash | |
| 5,304,349 A | 4/1994 | Polaschegg | |
| 5,409,612 A | 4/1995 | Maltais et al. | |
| 5,421,813 A | 6/1995 | Ohnishi | |
| 5,536,412 A | 7/1996 | Ash | |
| 5,589,070 A | 12/1996 | Maltais et al. | |
| 5,591,344 A | 1/1997 | Kenley et al. | |
| 5,603,902 A | 2/1997 | Maltais et al. | |
| 5,605,630 A | 2/1997 | Shibata | |
| 5,620,608 A | 4/1997 | Rosa et al. | |
| 5,643,212 A | 7/1997 | Coutre et al. | |
| 5,713,125 A | 2/1998 | Watanabe et al. | |
| 5,788,099 A | 8/1998 | Treu et al. | |
| 5,919,369 A | 7/1999 | Ash | |
| 5,944,684 A | 8/1999 | Roberts et al. | |
| 6,000,567 A | 12/1999 | Carlsson et al. | |
| 6,036,858 A | 3/2000 | Carlsson et al. | |
| 6,086,753 A | 7/2000 | Ericson et al. | |
| 6,143,181 A | 11/2000 | Falkvall et al. | |
| 6,170,785 B1 | 1/2001 | Lampropoulos et al. | |
| 6,188,407 B1 | 2/2001 | Smith et al. | |
| 6,190,855 B1 | 2/2001 | Herman et al. | |
| 6,277,277 B1 | 8/2001 | Jacobi et al. | |
| 6,280,632 B1 | 8/2001 | Polaschegg | |
| 6,308,721 B1 | 10/2001 | Bock et al. | |
| 6,409,699 B1 | 6/2002 | Ash | |
| 6,416,293 B1 | 7/2002 | Bouchard et al. | |
| 6,428,706 B1 | 8/2002 | Rosenqvist et al. | |
| 6,627,164 B1 | 9/2003 | Wong | |
| 6,755,976 B2 | 6/2004 | Rosenqvist et al. | |
| 6,818,196 B2 | 11/2004 | Wong | |
| 6,878,283 B2 | 4/2005 | Thompson | |
| 7,033,498 B2 | 4/2006 | Wong | |
| 7,077,956 B2 | 7/2006 | Rovatti | |
| 7,101,519 B2 | 9/2006 | Wong | |
| 7,169,303 B2 | 1/2007 | Sullivan et al. | |
| 7,241,272 B2 | 7/2007 | Karoor et al. | |
| 7,273,465 B2 | 9/2007 | Ash | |
| 7,566,432 B2 | 7/2009 | Wong | |
| 7,867,214 B2 | 1/2011 | Childers et al. | |
| 8,029,454 B2 | 10/2011 | Kelly et al. | |
| 2002/0079695 A1 | 6/2002 | Campbell et al. | |
| 2004/0019312 A1 | 1/2004 | Childers et al. | |
| 2004/0022717 A1 | 2/2004 | Wong | |
| 2004/0050789 A1 | 3/2004 | Ash | |
| 2005/0031523 A1 | 2/2005 | Wong | |
| 2005/0131332 A1 | 6/2005 | Kelly et al. | |
| 2005/0274658 A1 | 12/2005 | Rosenbaum et al. | |
| 2007/0158247 A1 | 7/2007 | Carr et al. | |
| 2007/0158249 A1 | 7/2007 | Ash | |
| 2007/0158268 A1 | 7/2007 | DeComo | |
| 2007/0161113 A1 | 7/2007 | Ash | |
| 2007/0161941 A1 | 7/2007 | Ash et al. | |
| 2007/0179431 A1 | 8/2007 | Roberts et al. | |
| 2007/0181499 A1 | 8/2007 | Roberts et al. | |
| 2008/0149563 A1 | 6/2008 | Ash | |
| 2008/0177216 A1 | 7/2008 | Ash | |
| 2009/0037216 A1 | 2/2009 | Bluemler et al. | |
| 2009/0127193 A1 * | 5/2009 | Updyke et al. | 210/636 |
| 2011/0000832 A1 | 1/2011 | Kelly et al. | |
| 2011/0004351 A1 | 1/2011 | Kelly et al. | |
| 2011/0005986 A1 | 1/2011 | Kelly et al. | |
| 2011/0005992 A1 | 1/2011 | Kelly et al. | |
| 2011/0009797 A1 | 1/2011 | Kelly et al. | |
| 2011/0009798 A1 | 1/2011 | Kelly et al. | |
| 2011/0017665 A1 * | 1/2011 | Updyke et al. | 210/638 |
| 2011/0105983 A1 | 5/2011 | Kelly et al. | |
| 2011/0160637 A1 * | 6/2011 | Beiriger | 604/6.11 |
| 2011/0297593 A1 | 12/2011 | Kelly et al. | |
| 2011/0303588 A1 | 12/2011 | Kelly et al. | |
| 2012/0018378 A1 | 1/2012 | Kelly et al. | |
| 2012/0022441 A1 | 1/2012 | Kelly et al. | |
| 2012/0043279 A1 | 2/2012 | Kelly et al. | |

FOREIGN PATENT DOCUMENTS

| | | |
|---|---|---|
| EP | 1096991 | 5/2001 |
| EP | 1342480 | 9/2003 |
| EP | 2087916 | 8/2009 |
| GB | 2124511 | 2/1984 |
| WO | 9702055 | 1/1997 |
| WO | 9702056 | 1/1997 |
| WO | 9817333 | 4/1998 |
| WO | 9937342 | 7/1999 |
| WO | 0230267 | 4/2002 |
| WO | 0243859 | 6/2002 |
| WO | 2004009158 | 1/2004 |
| WO | 2004105589 | 12/2004 |
| WO | 2005044339 | 5/2005 |
| WO | 2005123230 | 12/2005 |
| WO | 2007028056 | 3/2007 |
| WO | 2007081383 | 7/2007 |
| WO | 2007081384 | 7/2007 |
| WO | 2007081565 | 7/2007 |
| WO | 2007081576 | 7/2007 |

OTHER PUBLICATIONS

"Sorbent Dialysis Primer," COBE Renal Care, Inc., Sep. 4, 1993 Ed. 4.

Blumenkrantz, et al., "Applications of the Redy Sorbent System to Hemodialysis and Peritoneal Dialysis;" Artificial Organs, 3(3):230-236, 1978.

Operator's Manual—Fresenius 2008K Hemodialysis Machine (2000).

International Search Report and Written Opinion issued on May 14, 2013 in related International Application No. PCT/US2012/065248.

International Search Report and Written Opinion issued on Aug. 28, 2012 in related International Application No. PCT/US2011/052742.

* cited by examiner

SYSTEMS AND METHODS FOR COMPENSATION OF COMPLIANT BEHAVIOR IN REGENERATIVE DIALYSIS SYSTEMS

BACKGROUND

Contemporary regenerative dialysis systems enjoy widespread application. In such systems, a sorbent cartridge filters and regenerates dialysate fluid that is pumped between the dialysis equipment and the patient in a closed-loop path. Tap water can be used to prime the system with fluid. Dialysate is generated in an initial purification process using the sorbent cartridge. Typically, six liters of purified dialysate fluid is sufficient for performing a dialysis procedure.

During the dialysis procedure, the purified dialysate is continually pumped into a dialyzer chamber at an input pump. In the dialyzer chamber, the purified dialysate interacts with the patient's blood at a membrane, where urea particles are transferred from the blood into the dialysate. An output pump draws used dialysate from the dialyzer chamber at an output pump. The used dialysate is pumped through the sorbent cartridge, the chemistry of which is configured to filter and remove the urea particles from the dialysate, thereby purifying the dialysate.

Fluid is removed from a patient over a defined time period during the dialysis procedure. The rate at which the fluid is removed is referred to as the ultrafiltration rate. The ultrafiltration rate of a dialysis procedure is prescribed by a physician, and any variation from the prescribed ultrafiltration rate can result in serious adverse consequences to the patient. It is critical that the ultrafiltration rate remain positive during a procedure so that fluids are removed from the patient. At no time during the procedure should the ultrafiltration rate be negative; such "back-filtration" would result in the delivery of fluid to the patient through the dialyzer.

In regenerative dialysis systems, the ultrafiltration rate is a function of the pumping rate of the input pump, pumping purified dialysate into the dialyzer chamber, relative to the pumping rate of the output pump, pumping used dialysate from the dialyzer chamber. By controlling the relative input pump and output pump rates so that the output pump rate exceeds the input pump rate, the differential between the rates guarantees that fluid is removed from the patient.

Management of the ultrafiltration rate is paramount to a successful and safe dialysis procedure for the patient.

SUMMARY

In one aspect, a regenerative dialysis system includes an input pump that pumps fresh dialysate fluid into a dialyzer at an input rate. An output pump pumps used dialysate fluid from the dialyzer at an output rate. An ultrafiltration rate of the system is related to the output rate relative to the input rate. A sorbent cartridge filters the used dialysate fluid to generate the fresh dialysate fluid. A controller controls the ultrafiltration rate of the system in response to a flow rate of the dialysate fluid through the sorbent cartridge.

In one embodiment, the system further comprises: a reservoir that stores the fresh dialysate fluid; and a scale that monitors a scale weight of the fresh dialysate fluid stored in the reservoir; wherein the controller further controls the ultrafiltration rate in response to the scale weight of the fresh dialysate fluid in the reservoir.

In another embodiment, the controller further: calculates a dynamic weight of dialysate fluid stored in the sorbent cartridge in response to the flow rate of the dialysate fluid through the sorbent cartridge; calculates a corrected dialysate fluid weight by summing the dynamic weight and the scale weight; and controls the ultrafiltration rate of the system in response to the corrected dialysate fluid weight.

In another embodiment, the controller further: calculates an absorption weight of dialysate fluid stored in the sorbent cartridge as a result of time-based absorption; and calculates the corrected dialysate fluid rate by further summing the absorption weight with the dynamic weight and the scale weight.

In another embodiment, the controller controls the ultrafiltration rate of the system in response to the flow rate of the dialysate fluid through the sorbent cartridge based on a predefined model of compliant behavior by the sorbent cartridge.

In another embodiment, the predefined model of the sorbent cartridge is based on a relationship between a volume of dialysate fluid stored by the sorbent cartridge as a function of flow rate of the dialysate fluid through the sorbent cartridge.

In another embodiment, the relationship between the volume of dialysate fluid stored by the sorbent cartridge as a function of flow rate of the dialysate fluid through the sorbent cartridge is linear.

In another embodiment, the relationship between the volume of dialysate fluid stored by the sorbent cartridge as a function of flow rate of the dialysate fluid through the sorbent cartridge is non-linear.

In another embodiment, the ultrafiltration rate is a rate at which fluid is removed from a patient at the dialyzer.

In another embodiment, the ultrafiltration rate of a dialysis procedure performed by the dialysis system is prescribed.

In another aspect, a method of controlling ultrafiltration rate of a regenerative dialysis system comprises: pumping fresh dialysate fluid into a dialyzer at an input rate; pumping used dialysate fluid from the dialyzer at an output rate, an ultrafiltration rate of the regenerative dialysis system being related to the output rate relative to the input rate; filtering the used dialysate fluid to generate the fresh dialysate fluid at a sorbent cartridge; and controlling the ultrafiltration rate of the regenerative dialysis system in response to a flow rate of the dialysate fluid through the sorbent cartridge.

In one embodiment, the method further comprises: storing the fresh dialysate fluid at a reservoir; monitoring a scale weight of the fresh dialysate fluid stored in the reservoir; and further controlling the ultrafiltration rate in response to the scale weight of the fresh dialysate fluid in the reservoir.

In another embodiment, the method further comprises: calculating a dynamic weight of dialysate fluid stored in the sorbent cartridge in response to the flow rate of the dialysate fluid through the sorbent cartridge; calculating a corrected dialysate fluid weight by summing the dynamic weight and the scale weight; and further controlling the ultrafiltration rate in response to the corrected dialysate fluid weight.

In another embodiment, the method further comprises: calculating an absorption weight of dialysate fluid stored in the sorbent cartridge as a result of time-based absorption; and calculating the corrected dialysate fluid rate by further summing the absorption weight with the dynamic weight and the scale weight.

In another embodiment, the method further comprises controlling the ultrafiltration rate of the system in response to the flow rate of the dialysate fluid through the sorbent cartridge based on a predefined model of compliant behavior by the sorbent cartridge.

In another embodiment, the predefined model of the sorbent cartridge is based on a relationship between a volume of dialysate fluid stored by the sorbent cartridge as a function of flow rate of the dialysate fluid through the sorbent cartridge.

In another embodiment, the relationship between the volume of dialysate fluid stored by the sorbent cartridge as a function of flow rate of the dialysate fluid through the sorbent cartridge is linear.

In another embodiment, the relationship between the volume of dialysate fluid stored by the sorbent cartridge as a function of flow rate of the dialysate fluid through the sorbent cartridge is non-linear.

In another embodiment, the ultrafiltration rate is a rate at which fluid is removed from a patient at the dialyzer.

In another embodiment, ultrafiltration rate of a dialysis procedure performed by the regenerative dialysis system is prescribed.

In another aspect, a controller comprises a plurality of function modules stored in a storage system and executable by a processor to control an ultrafiltration rate of a regenerative dialysis system. The controller comprises: an input pump function module that outputs an input pump control signal effecting the pumping of fresh dialysate fluid into a dialyzer at an input rate; an output pump function module that outputs an output pump control signal effecting the pumping of used dialysate fluid from the dialyzer at an output rate, an ultrafiltration rate of the regenerative dialysis system being related to the output rate relative to the input rate, whereby the used dialysate fluid is filtered at a sorbent cartridge to generate the fresh dialysate fluid; and an ultrafiltration rate function module that controls the ultrafiltration rate of the regenerative dialysis system in response to a flow rate of the dialysate fluid through the sorbent cartridge.

In one embodiment, the ultrafiltration rate function module further comprises a scale weight sampler function module that monitors a scale weight of the fresh dialysate fluid stored in a reservoir, wherein the ultrafiltration rate function module further controls the ultrafiltration rate in response to the scale weight of the fresh dialysate fluid in the reservoir.

In another embodiment, the ultrafiltration rate function module further comprises: a dynamic weight calculation function module that calculates a dynamic weight of dialysate fluid stored in the sorbent cartridge in response to the flow rate of the dialysate fluid through the sorbent cartridge; and a weight correction function module that calculates a corrected dialysate fluid weight by summing the dynamic weight and the scale weight, wherein the ultrafiltration rate function module further controls the ultrafiltration rate in response to the corrected dialysate fluid weight.

In another embodiment, the ultrafiltration rate function module further comprises an absorption weight calculation function module that calculates an absorption weight of dialysate fluid stored in the sorbent cartridge as a result of time-based absorption, wherein the weight correction function module calculates the corrected dialysate fluid rate by further summing the absorption weight with the dynamic weight and the scale weight.

In another embodiment, the ultrafiltration rate function module further controls the ultrafiltration rate of the system in response to the flow rate of the dialysate fluid through the sorbent cartridge based on a predefined model of compliant behavior by the sorbent cartridge.

In another embodiment, the predefined model of the sorbent cartridge is based on a relationship between a volume of dialysate fluid stored by the sorbent cartridge as a function of flow rate of the dialysate fluid through the sorbent cartridge.

In another embodiment, the relationship between the volume of dialysate fluid stored by the sorbent cartridge as a function of flow rate of the dialysate fluid through the sorbent cartridge is linear.

In another embodiment, the relationship between the volume of dialysate fluid stored by the sorbent cartridge as a function of flow rate of the dialysate fluid through the sorbent cartridge is non-linear.

In another embodiment, the ultrafiltration rate is a rate at which fluid is removed from a patient at the dialyzer.

In another embodiment, the ultrafiltration rate of a dialysis procedure performed by the regenerative dialysis system is prescribed.

BRIEF DESCRIPTION OF THE DRAWINGS

The foregoing and other objects, features and advantages of the embodiments of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the embodiments of the invention.

DETAILED DESCRIPTION OF EMBODIMENTS

Embodiments will now be described more fully hereinafter with reference to the accompanying drawings, in which preferred embodiments of the invention are shown. This invention may, however, be embodied in different forms and should not be construed as limited to the embodiments set forth herein. Like numbers refer to like elements throughout the specification.

It will be understood that, although the terms "first", "second", etc. are used herein to describe various elements, these elements should not be limited by these terms. These terms are used to distinguish one element from another. For example, a "first" element could be termed a "second" element, and, similarly, a "second" element could be termed a "first" element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element, or intervening elements can be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments and is not intended to be limiting of the invention. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Figure 1:
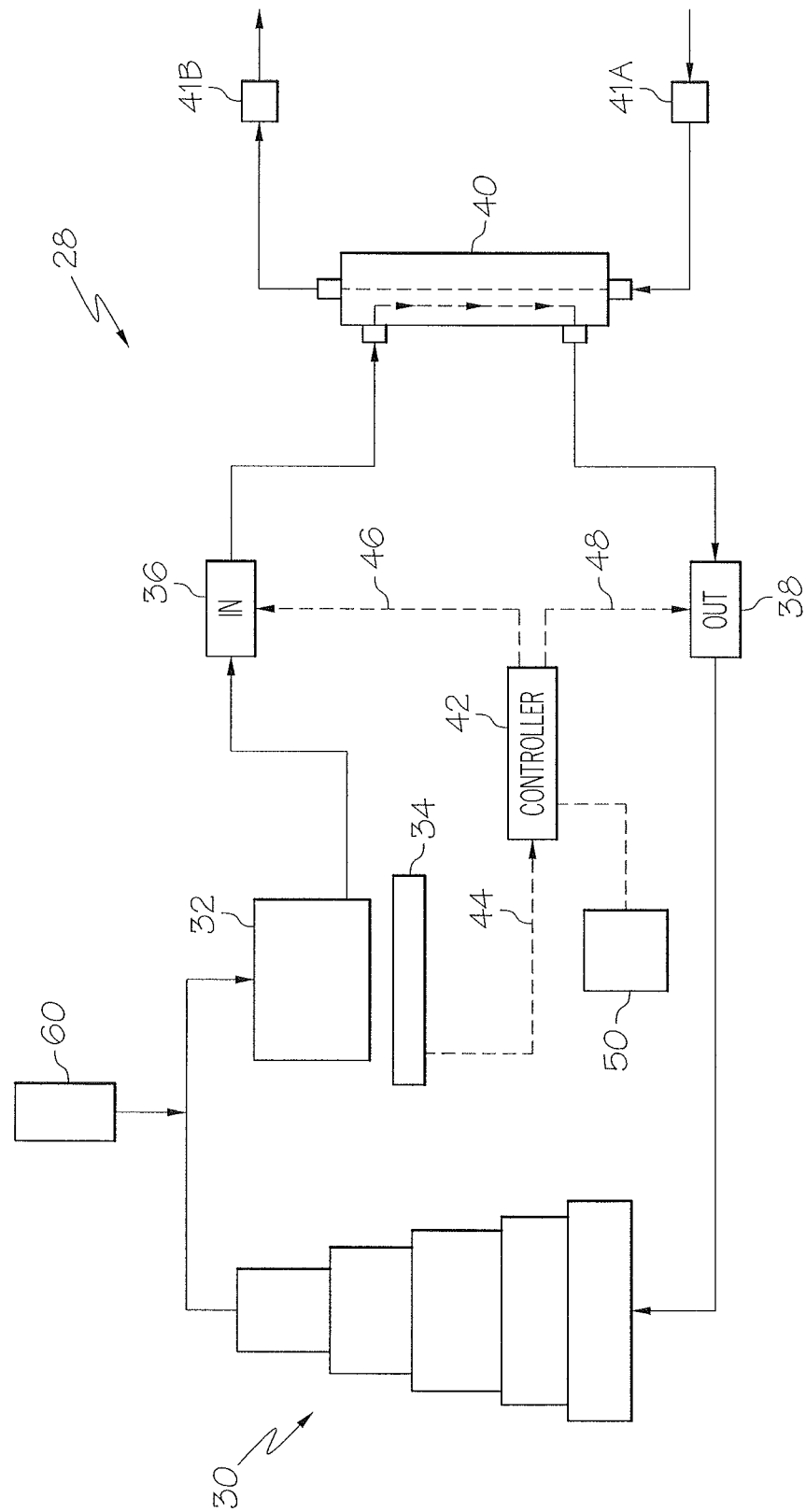
FIG. 1 is a block diagram of a regenerative dialysis system in accordance with embodiments of the present invention.

FIG. 1 is a block diagram of a regenerative dialysis system in accordance with embodiments of the present invention. A regenerative dialysis system 28 in accordance with the present embodiment comprises a dialyzer 40, an output pump 38, a sorbent cartridge 30, a dialysate reservoir 32, a scale 34, and an input pump 36.

The output pump 38 is coupled to an output of the dialyzer 40 and receives and pumps used dialysate fluid from the dialyzer 40 at an output rate. Used dialysate fluid is pumped from the output pump 38 to an input of the sorbent cartridge 30.

The used dialysate fluid progresses through multiple layers of the sorbent cartridge 30, each layer having a specified chemistry. The respective multiple layers operate to further purify the used dialysate in stages. Details of the reaction that occurs in the sorbent cartridge 30 will be discussed in further detail below.

Fresh dialysate fluid is provided at an output of the sorbent cartridge 30 and proceeds to the dialysate reservoir 32, where it is stored for further processing. Infusate 60 is added to the fresh dialysate fluid output by the sorbent cartridge at a prescribed rate during a dialysis procedure in accordance with well-established techniques, so that the dialysate fluid presented to the patient in the course of the procedure has a suitable chemistry.

The input pump 36 draws stored fresh dialysate fluid from the dialysate reservoir 32 and pumps the fresh dialysate fluid into the dialyzer 40 at an input rate. In the dialyzer 40, the fresh dialysate fluid interacts with the patient's blood at a membrane, and urea particles are transferred from the blood into the dialysate. The blood enters the dialyzer 40 at an input port 41A and exits at an output port 41B. The used dialysate fluid is pumped from the dialyzer 40 at an output rate, as described above.

Fluid is removed from a patient over a defined time period during a dialysis procedure. The rate at which the fluid is removed is referred to as the ultrafiltration rate.

The ultrafiltration rate of a dialysis procedure is prescribed by a physician, and any variation from the prescribed ultrafiltration rate can result in serious adverse consequences to the patient. It is critical that the ultrafiltration rate remain positive during a procedure so that fluids are removed from the patient. At no time during the procedure should the ultrafiltration rate be negative, which would result in the delivery of fluid to the patient through the dialyzer 40. Such "backfiltration" can be harmful to the patient, and is to be avoided.

The ultrafiltration rate of the dialysis system 28 is controlled by managing the output rate of the output pump 38 relative to the input rate of the input pump 36. By controlling the respective rates of the output pump 38 and the input pump 36 so that the output rate of the output pump 38 exceeds the input rate of the input pump 36, a positive ultrafiltration rate can be achieved, ensuring that fluid is drawn from the patient at the dialyzer 40, and not the reverse.

Excess fluid that is drawn by the output pump 38 from the dialyzer 40 in accordance with the ultrafiltration rate is combined with the used dialysate and purified by the sorbent cartridge 30, where it is regenerated and stored in the dialysate reservoir 32. The excess fluid is accumulated over time in the dialysate reservoir 32 in accordance with the ultrafiltration rate. The amount of excess fluid drawn and accumulated in the dialysate reservoir can be monitored according to its weight by a scale 34.

The scale 34 is configured to measure the weight of the dialysate reservoir 32 at regular intervals. The progress of a dialysis procedure can be precisely monitored by tracking the weight of dialysate reservoir over time, to ensure that an appropriate amount of fluid is being pulled from the patient at an appropriate rate. If a variation from the prescribed ultrafiltration rate is determined, any necessary adjustments can be made to the dialysis system, for example, either manually, by an attendant, or, in recent systems, automatically, by a control system.

In certain embodiments, the system ultrafiltration rate can be managed automatically, by an automated control system. In such a system, a controller 42 receives a weight signal 44 from the scale 34, the weight signal 44 being indicative of the present actual weight of the dialysate reservoir 32. The controller 42 can also include a timer that tracks the elapsed time of the procedure or that tracks the time elapsed since the previous scale weight sample. The controller further provides an output rate signal 48 to the output pump 38, and an input rate signal 46 to the input pump 36.

Since the weight of the empty dialysate reservoir 32 is known, this weight can be discriminated from the calculation of the weight of the dialysate in the reservoir. Further since the chemistry and density of the dialysate used in the procedure are known, the volume of the dialysate present in the dialysate reservoir 32 can be accurately derived from its weight. By comparing the actual weight of the dialysate reservoir to an expected weight that is derived from a prescribed ultrafiltration rate, and by monitoring the elapsed time of the procedure and/or the time between weight samples, the controller 42 can determine whether any variation in the ultrafiltration rate of the procedure has occurred. In the event such a variation outside prescribed limits has occurred, the controller 42 can, for example, increase the ultrafiltration rate, or decrease the ultrafiltration rate, for a specified time period.

In one example, the controller 42 can cause an increase in the ultrafiltration rate by increasing the difference between the output rate of the output pump 38 and the input rate of the input pump 36. In response to such an increase, the dialysis system 28 will draw relatively more fluid from the patient over time. In another example, the controller 42 can cause a decrease in the ultrafiltration rate by decreasing the difference between the output rate of the output pump 38 and the input rate of the input pump 36. In response to such an decrease, the dialysis system 28 will draw relatively less fluid from the patient over time.

It has been determined that certain components of the regenerative dialysis systems behave with compliance, in the sense that the amount of fluid they contain at any time is dependent on the dialysate flow rate of the dialysate fluid passing through them. For example, it has been demonstrated that the sorbent cartridge 30, in particular, demonstrates compliance behavior.

In one example, the dialysate flow rate of the regenerative dialysis system 28 is determined to be the flow rate of dialysate fluid as processed by the output pump 38, which is equal to the rate of flow of the dialysate fluid through the sorbent cartridge 30. It has been determined that the amount of fluid stored by the sorbent cartridge 30 changes in a manner that corresponds with a change in the dialysate flow rate through the sorbent cartridge 30. In general, as the dialysate flow rate increases, the amount of additional fluid stored in the sorbent cartridge 30 increases.

Such an increased dialysate flow rate through the sorbent cartridge 30 results in an increased internal pressure in the sorbent cartridge 30, in turn compressing air pockets in the sorbent cartridge 30. With such compression, there is additional space in the sorbent cartridge 30 for the storage of additional fluid. Also, with increased pressure, swelling of the plastic shell of the sorbent cartridge can occur, further increasing the volume of fluid stored in the cartridge. Assuming that the increase in dialysate flow rate occurs during a dialysis procedure, a corresponding reduced amount of fluid will be stored in the dialysate reservoir 32, since the displaced fluid is instead stored in the sorbent cartridge 30. Accordingly, the weight signal 44 output by the scale 34 will indicate the presence of relatively less fluid in the dialysate reservoir 32. A portion of the dialysate fluid formerly stored in the dialysate reservoir 32 would then be displaced to, and stored in, the sorbent cartridge 30. As a result, the weight of the dialysate reservoir 32 as indicated by the weight signal 44 output by the scale 34 is no longer properly indicative of the cumulative amount of fluid present in the dialysis system 28; therefore the weight signal 44 is no longer properly indicative of the cumulative amount of fluid drawn from the patient during the procedure. Under this scenario, the controller 42 will operate under the erroneous belief that the ultrafiltration rate of the procedure is too low, and may incorrectly adjust the relative fluid rates of the input pump 36 and output pump 38 to increase the ultrafiltration rate.

Similarly, as the dialysate flow rate decreases, the amount of fluid stored in the sorbent cartridge 30 decreases. A decreased dialysate flow rate through the sorbent cartridge 30 results in an decreased internal pressure in the sorbent cartridge 30, in turn decompressing air pockets in the sorbent cartridge 30. With such decompression, there is reduced space in the sorbent cartridge 30 for the storage of additional fluid. Assuming that the decrease in dialysate flow rate occurs during a dialysis procedure, a corresponding increased amount of fluid will be stored in the dialysate reservoir 32, since the fluid is displaced from the sorbent cartridge 30 to the dialysate reservoir 32. Accordingly, the weight signal 44 output by the scale 34 will indicate the presence of relatively more fluid in the dialysate reservoir 32. A portion of the dialysate fluid formerly stored in the sorbent cartridge 30 would then be displaced to, and stored in, the dialysate reservoir 32. As a result, the weight of the dialysate reservoir 32 as indicated by the weight signal 44 output by the scale 34 is no longer properly indicative of the amount of fluid present in the dialysis system 28; therefore the weight signal 44 is no longer properly indicative of the cumulative amount of fluid drawn from the patient during the procedure. Under this scenario, the controller 42 will operate under the erroneous belief that the ultrafiltration rate of the procedure is too high, and may incorrectly adjust the relative fluid rates of the input pump 36 and output pump 38 to decrease the ultrafiltration rate.

Such an increase or decrease in the ultrafiltration rate by the controller during a dialysis procedure based on false information can cause severe injury to the patient. An erroneous increase in the ultrafiltration rate by the controller 42 can lead to excessive fractional-filtration, causing excessive hempconcentration, clotting, or hemolysis in the patient. An erroneous decrease in the ultrafiltration rate by the controller 42 can lead to back-filtration, or the excessive discharge of fluid from the dialysis machine into the patient.

Embodiments of the present invention compensate for compliant behavior in the sorbent cartridge of a regenerative dialysis system. Further embodiments compensate for compliant behavior in other components of a regenerative dialysis system.

In one embodiment, the compliant behavior of the sorbent cartridge 30 can be modeled in response to fluid flow rate through the sorbent cartridge 30. A compliance model 50 of the sorbent cartridge 30 is made available to the controller 42 during a dialysis procedure. In this manner, the controller 42 can make decisions with regard to control of ultrafiltration rate of the regenerative dialysis system 28 based on the present dialysate flow rate through the sorbent cartridge 30, and based on the compliance model 50 of the sorbent cartridge. In a case where the ultrafiltration rate of the regenerative dialysis system 28 is determined in response to the respective output rate of the output pump 38 and the input rate of the input pump 36, the controller 42 can make decisions with regard to ultrafiltration rate of the regenerative dialysis system 28 by making adjustments to the input rate signal 46 to the input pump 36 and to the output rate signal 48 to the output pump 38 based on the present dialysate flow rate through the sorbent cartridge, and based on the compliance model 50 of the sorbent cartridge.

It has been determined that the compliant behavior of the sorbent cartridge 30 can be linear, in the sense that the amount of additional fluid stored by the sorbent cartridge as a result of compliance increases substantially linearly in response to increased dialysate flow rate through the sorbent cartridge 30.

Figure 2:
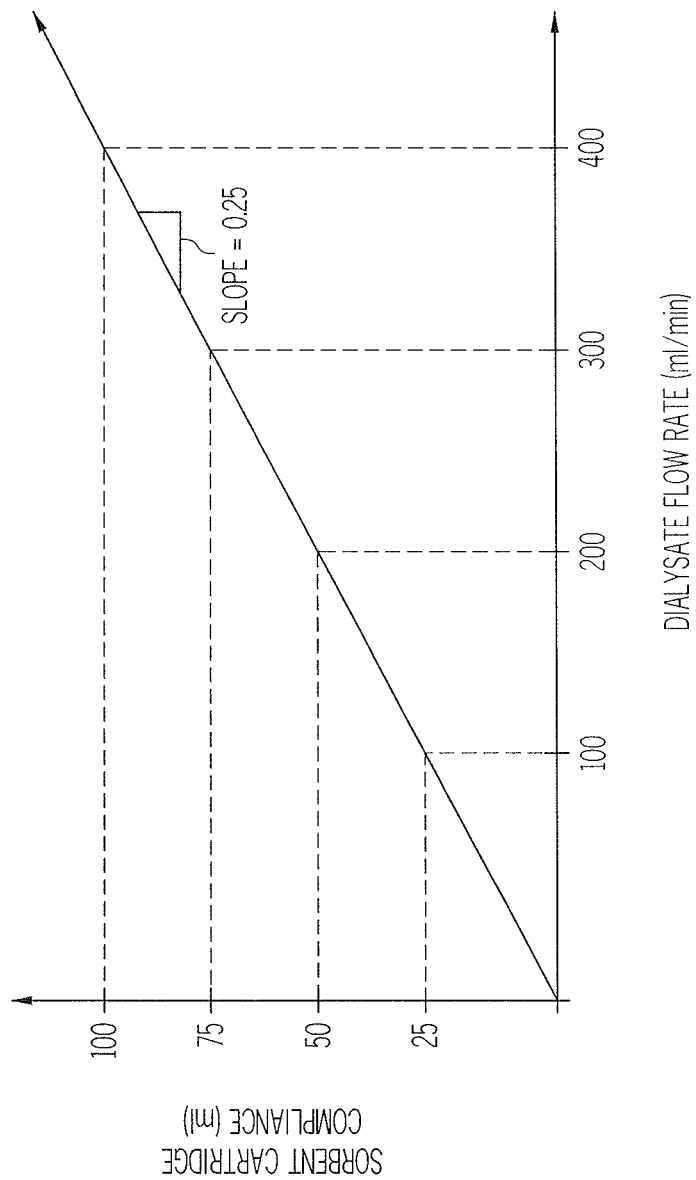
FIG. 2 is an example graph of sorbent cartridge compliance as a function of dialysate flow rate.

FIG. 2 is an example graph of sorbent cartridge compliance as a function of dialysate flow rate. In this example, it can be assumed that the amount of additional dialysate fluid stored by the sorbent cartridge 30 increased by a factor of 0.25 as dialysate flow rate increased. For example, at a dialysate flow rate of 0 ml/min, the additional dialysate fluid stored by the sorbent cartridge 30 was 0 ml. At a dialysate flow rate of 100 ml/min, the additional dialysate fluid stored by the sorbent cartridge 30 was approximately 25 ml. At a dialysate flow rate of 200 ml/min, the additional dialysate fluid stored by the sorbent cartridge 30 was approximately 50 ml. At a dialysate flow rate of 300 ml/min, the additional dialysate fluid stored by the sorbent cartridge 30 was approximately 75 ml. At a dialysate flow rate of 400 ml/min, the additional dialysate fluid stored by the sorbent cartridge 30 was approximately 100 ml.

Under such a linear model of compliant behavior, the model 50 can be a single linear factor, such as 0.25 in the example above, that can be applied to the controller to make decisions with regard to ultrafiltration rate. As the dialysate flow rate is adjusted, the amount of fluid stored in the sorbent cartridge is known to the controller, based on the linear factor.

In other embodiments, the model of compliant behavior of the sorbent cartridge 30 can be a non-linear, higher-order model, such as a second-order or third order-polynomial, depending on the level of precision required. In these embodiments, the dialysate flow rate is input into the second-order or third-order system to estimate compliance in the sorbent cartridge as a function of dialysate flow rate.

In various embodiments, the model 50 can comprise any of a number of systems for calculating sorbent cartridge compliance as a function of dialysate flow rate. For example, the model 50 can comprise a first-order, second-order, or higher-order equation embodied in software operating on in connection with processor, firmware, or digital or analog hardware. In other embodiments, the model 50 can comprise a digital or analog filter embodied in software operating on a processor, firmware, or digital or analog hardware. In other embodiments, the model 50 can comprise a look-up table embedded in volatile or non-volatile memory accessible by the controller 42.

Although the model 50 is shown as a unit that is separate from the controller 42 in the block diagram of FIG. 1, for the purpose of illustration, in various embodiments, the model 50 can be integral with the controller 42, and reside on the controller in memory, software, firmware or hardware.

Figure 3:
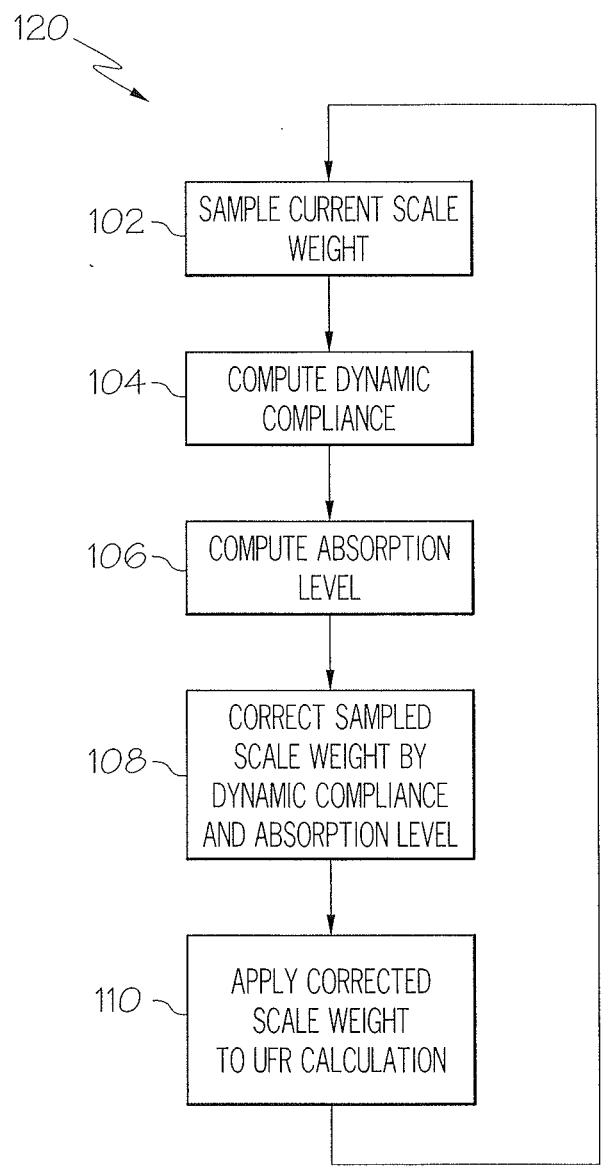
FIG. 3 is a flow diagram of the operation of a compensation system in accordance with embodiments of the present invention.

FIG. 3 is a flow diagram of the operation of a compensation system 120 in accordance with embodiments of the present invention. In one example embodiment, the compensation system 120 can be embodied as software operating on the controller 42 shown above in FIG. 1.

Referring to FIG. 3, a periodic sampling of the weight signal 44 output by the scale 32 is performed by the compensation system 120 at step 102. As described above, the weight signal 44 is representative of the volume of dialysate presently contained in the dialysate reservoir 32. In certain embodiments, the scale 34 comprises one or more load cells connected to a stainless steel plate. The scale 34 can be is calibrated to have a known mass, and the calibration values can be stored in a microcontroller that is local to the scale. Analog signal conditioning circuitry can be used to amplify and filter the analog signals output by the load cells and an analog-to-digital converter can digitize the output of the conditioned load cell signals. The local microcontroller can acquire the digitized signal from the analog-to-digital converter, for example using an SPI serial bus. The local microcontroller can sum the load cell outputs and apply the calibration parameters to the digitized signal and convert the resulting value into milligrams. In one embodiment, the load cell outputs from contiguous samples can be examined and applied to a median filter to eliminate any samplings that are outside of a particular range, such as 3 standard deviations from the mean sampling amount. Such an embodiment can help to eliminate noisy readings from affecting the resulting ultrafiltration rate. The local microcontroller can then send the converted value to the main controller 42. In an alternative embodiment, the digitized output of the load cell can be transmitted directly to the main controller 42 for processing and conversion.

At step 104, the compensation system 120 computes the dynamic compliance of the sorbent cartridge 30. As described above, the dynamic compliance of the sorbent cartridge 30 represents the amount of additional dialysate fluid that is stored in the sorbent cartridge 30 in response to the current dialysate flow rate of dialysate fluid through the sorbent cartridge 30. Details of step 104 will be described below in connection with the description of FIG. 5.

At step 106, the compensation system 120 also computes an absorption level of the sorbent cartridge 30. It has been shown that in addition to the dynamic compliant behavior exhibited by the sorbent cartridge 30 described above, the sorbent cartridge further exhibits an absorption which can also be referred to as a static compliant behavior. During a dialysis procedure, the sorbent cartridge 30 stores more dialysate as the elapsed time of the procedure increases. This is because the material of the sorbent cartridge becomes increasingly hydrated as the time of exposure to dialysate increases. This absorption behavior is generally independent of the dynamic compliance behavior; however, in certain cases, the dynamic compensation behavior can be dependent on the absorption behavior. For example, the change in sorbent cartridge compliance due to a flow rate change at an elapsed time of 1 hour into a procedure can be different than the change in compliance due to a flow rate change at an elapsed time of 3 hours into a procedure. The sorbent cartridge can thus behave less dynamically over time since, with greater saturation of the cartridge due to absorption as treatment time elapses, there is proportionally less material in the sorbent cartridge that will behave with compliance. Details of step 106 will be described below in connection with the description of FIG. 6.

Figure 4:
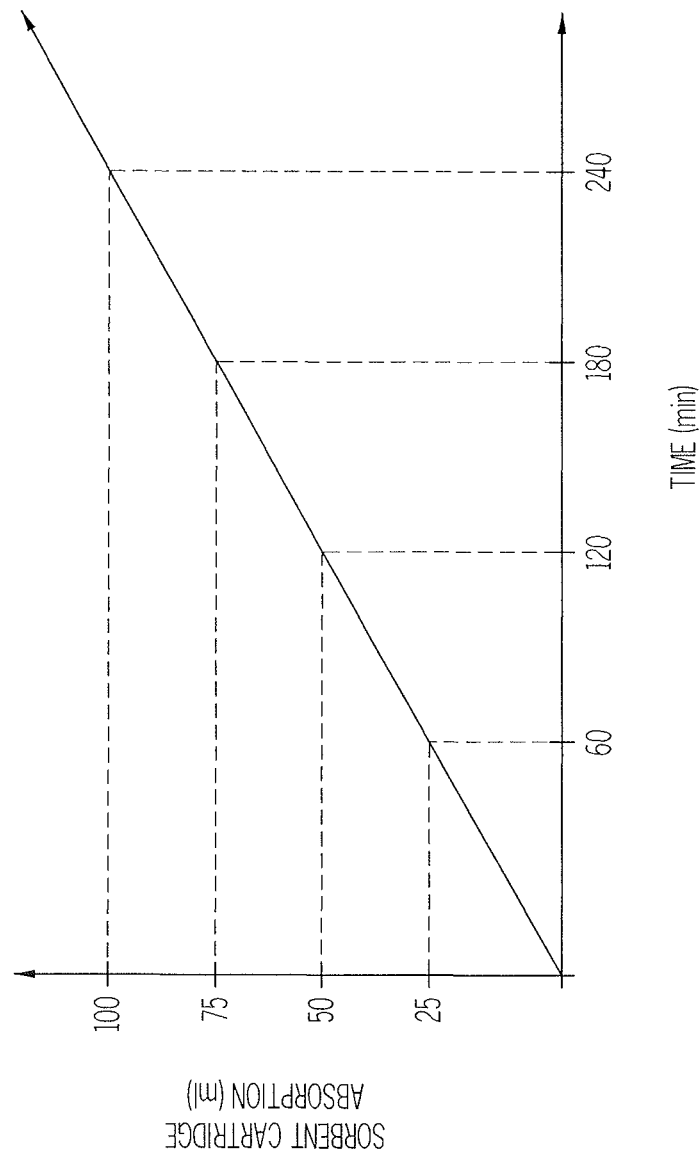
FIG. 4 is an example graph of sorbent cartridge absorption as a function of time.

FIG. 4 is an example graph of sorbent cartridge absorption as a function of time. In this example, it can be seen that as the time of the procedure progresses, the additional amount of dialysate fluid stored in the sorbent cartridge as a result of absorption increases. For example, at a time of 0 minutes, while the sorbent cartridge is considered to be saturated, the additional dialysate fluid stored by the sorbent cartridge 30 as a result of absorption is 0 ml. At a time of 60 minutes, the additional dialysate fluid stored by the sorbent cartridge 30 as a result of absorption is approximately 25 ml. At a time of 120 minutes, the additional dialysate fluid stored by the sorbent cartridge 30 as a result of absorption is approximately 50 ml. At a time of 180 minutes, the additional dialysate fluid stored by the sorbent cartridge 30 as a result of absorption is approximately 75 ml. At a time of 240 minutes, the additional dialysate fluid stored by the sorbent cartridge 30 as a result of absorption is approximately 100 ml. Based on the graph of FIG. 4, it is apparent that absorption behavior in the sorbent cartridge can be modeled as a linear relationship. For example, the absorption model 50 can be a single, linear factor, such as 0.416 ml/min, in the example above, that can be applied by the controller 42 to compensate for absorption. In other embodiments, the absorption model can be a higher-order model, such as a second-order or third-order model, depending on the level of precision required in the absorption determination.

Referring back to FIG. 3, at step 108, the compensation system 120 adjusts the sampled weight signal 44 sampled at step 102 by the dynamic compliance weight computed at step 104 and by the absorption weight calculated at step 106. A corrected scale weight is computed as a result of the adjustment. Details of step 108 will be described below in connection with the description of FIG. 7.

At step 110, the compensation system 120 applies the corrected scale weight to a ultrafiltration rate calculation unit. The ultrafiltration rate calculation unit calculates an updated ultrafiltration rate, and determines whether adjustments to the system ultrafiltration rate are needed. In one example embodiment, this operation is performed by a proportional integral derivative controller (PID) that continually monitors the measured ultrafiltration rate and compares that to a desired ultrafiltration rate. In this embodiment, the corrected scale weight is applied to the PID and, based on the known elapsed time of the dialysis procedure t, the current corrected scale weight $C(t)$ and a previous corrected scale weight $C(t-1)$, a measured ultrafiltration rate $UFR_m$ is determined. The PID periodically compares the measured ultrafiltration rate $UFR_m$ to a stored desired ultrafiltration rate $UFR_d$ and, if needed, adjusts the output rate signal 48 applied to the output pump 38, and/or the input rate signal 46 applied to the input pump 36 to vary their respective dialysate fluid pump rates.

The frequency of performing the sampling operation 102 and the computation and application steps 104, 106, 108, 110, can be controlled by the desired precision of the procedure, while weighing processor bandwidth considerations for performing the calculations. The above samplings and computation steps 102, 104, 106, 108, 110 can be performed in any of a number of different orders and are not limited to the specific order shown above in FIG. 3. For example, the scale weight can be sampled 102 at the same time the absorption level is being computed 106, and the dynamic compliance can then be calculated 104. Any of a number of different orderings are applicable to the embodiments of the present invention. In one example embodiment, the controller 42 can perform the computation and application steps 104, 106, 108, 110 each time a periodic sampling of the current scale weight 102 occurs, or, in an alternative embodiment, each time a number of samplings of the current scale weight 102 occurs.

Figure 5:
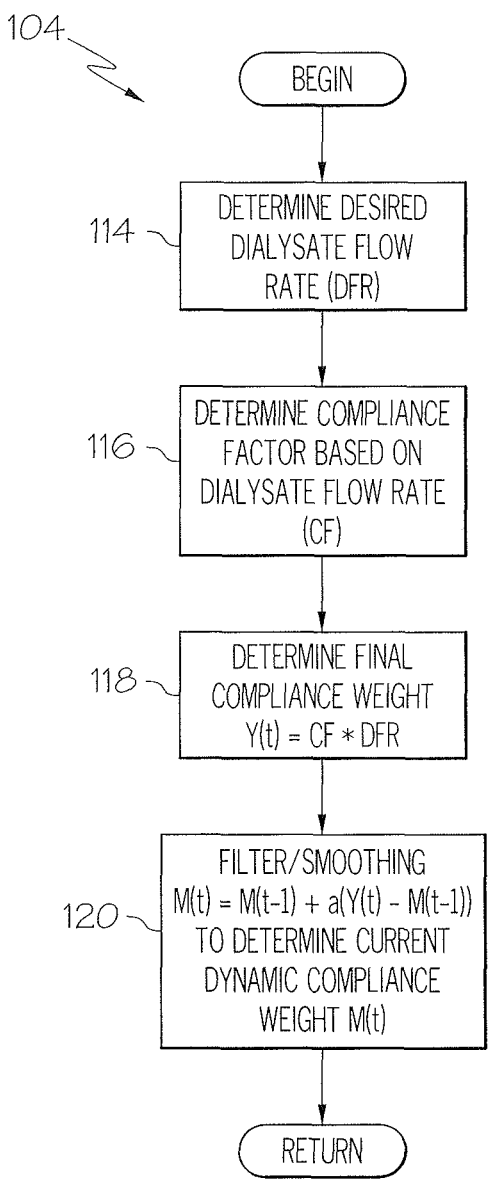
FIG. 5 is a detailed flow diagram of an operation for performing the step of computing dynamic compliance, in accordance with embodiments of the present invention.

FIG. 5 is a detailed flow diagram of an operation for performing the step 104 of computing dynamic compliance, in accordance with embodiments of the present invention. As described above, the dynamic compliance of the sorbent cartridge 30 represents the amount of additional dialysate fluid that is stored in the sorbent cartridge in response to the current dialysate flow rate of dialysate fluid through the sorbent cartridge 30.

In the embodiment of FIG. 5, a desired dialysate flow rate (DFR) is determined at step 114. This desired dialysate flow rate (DFR) is selected by the system attendant, or by a system computer. Typical desired dialysate flow rates include 200 ml/min, 300 ml/min and 400 ml/min, for example, A compliance factor (CF) of the sorbent cartridge 30 is determined based on the desired dialysate flow rate at step 116. In the example described above in connection with FIG. 2, the compliance factor (CF) of the sorbent cartridge is 0.25. Since the compliance model in the example is generally linear, the compliance remains at a factor of 0.25 throughout the range of typical dialysis flow rates (DFRs) between 0 and 400 ml/min.

A final compliance weight associated with the dialysate present in the sorbent cartridge is computed at step 118. In one embodiment, the final compliance weight Y(t) equals the product of the desired dialysate flow rate (DFR) and the compliance factor (CF):

$$Y(t)=CF*DFR \qquad (1a)$$

Although the present compliance factor of the sorbent cartridge is represented as a linear model, models of higher-order are equally applicable to the embodiments of the present invention, as described above. One example of such a non-linear relationship can be modeled according to the following relationship:

$$Y(t) = (R - DFR) + \left(L - \frac{\partial DFR}{\partial t}\right) + \frac{1}{C}\int_0^t DFR \partial t \qquad (1b)$$

where R, L and C are compliance factors for the system.

The current dynamic compliance weight M(t) is computed in step 120. In one embodiment, the computation is performed using an exponential filter. In one embodiment, the exponential filter provides a smoothing function, so that the current dynamic compliance weight M(t) exponentially approaches the final compliance weight Y(t) according to the relationship:

$$M(t)=M(t-1)+a(Y(t)-M(t-1)) \qquad (2)$$

In this relationship: M(t) represents the current dynamic compliance weight; M(t−1) is the first part of the equation and represents the previously computed dynamic compliance weight, that is, computed at the last iteration of the operation; a represents the compliance filter coefficient that is applied to the second part of the equation (Y(t)−M(t−1)); Y(t) is the final compliance weight, as computed above in step 118. The compliance filter coefficient a can vary between 0 and 1; if the coefficient a is zero or near-zero, full smoothing is applied to the current dynamic compliance weight M(t) calculation, whereas if the coefficient a is one or near one, no smoothing is applied to the current dynamic compliance weight M(t) calculation. The compliance filter coefficient a operates as a scaling or weighting of how much the difference between the final compliance weight Y(t) and the previously computed dynamic compliance weight M(t−1) is added to the previously computed dynamic compliance weight M(t−1) to provide the current dynamic compliance weight M(t). The compliance filter coefficient a can be for example, determined empirically by comparing the model to actual sorbent cartridge compliance measurements determined in the laboratory at various dialysate flow rates. A typical, nominal value for the filter coefficient a is 0.33.

In the above example embodiment of the dynamic compliance computation process 104, the dynamic compliance behavior model of the sorbent cartridge is determined empirically, in the laboratory. The thereby empirically determined model is applied to sorbent cartridges mounted to each system. The empirically determined model is thus fixed, or static, in the sense that the same model is applied to each sorbent cartridge applied to the system.

In another embodiment, a dynamic determination of the dynamic compliance behavior model can be performed. Such a dynamic determination takes into consideration differences between each individual sorbent cartridge, by pre-measuring the performance of a given cartridge on a given system, prior to a dialysis procedure. In this manner, the specific compliance behavior of each individual specific cartridge is considered and compensated for. In an example embodiment, a new sorbent cartridge is mounted to the system, and, during initialization, a change in fluid weight of the dialysate fluid present in the reservoir 32 on the scale 34 is determined as a result of a change in the dialysate flow rate. Multiple flow rates are tested and the scale weight is determined for each flow rate, and a compliance factor is determined as the change in scale weight relative to the change in flow rate.

In one example of a dynamic determination of the dynamic compliance behavior model, assuming a linear fluidic model, and, assuming that the sorbent cartridge behaves like a linear fluidic resistor, one can solve for the resistance value in the event that two distinct points on the resistance curve are known. By setting the dialysate flow rate to two unique flow rates, two points on the resistance curve can be determined. This, in turn, allows for a calculation of the slope of the curve, which corresponds to the linear resistance R. Knowing R for a specific cartridge, compensation of the scale weight for that specific cartridge can be achieved. Similarly, system identification can be used to calculate the coefficients of higher-order models of the system. For example, a ramp or triangle function corresponding to dialysate flow and the Fourier transform on recorded data can be used to determine the time constant of the system, and thus, its higher order coefficients can be determined.

Figure 6:
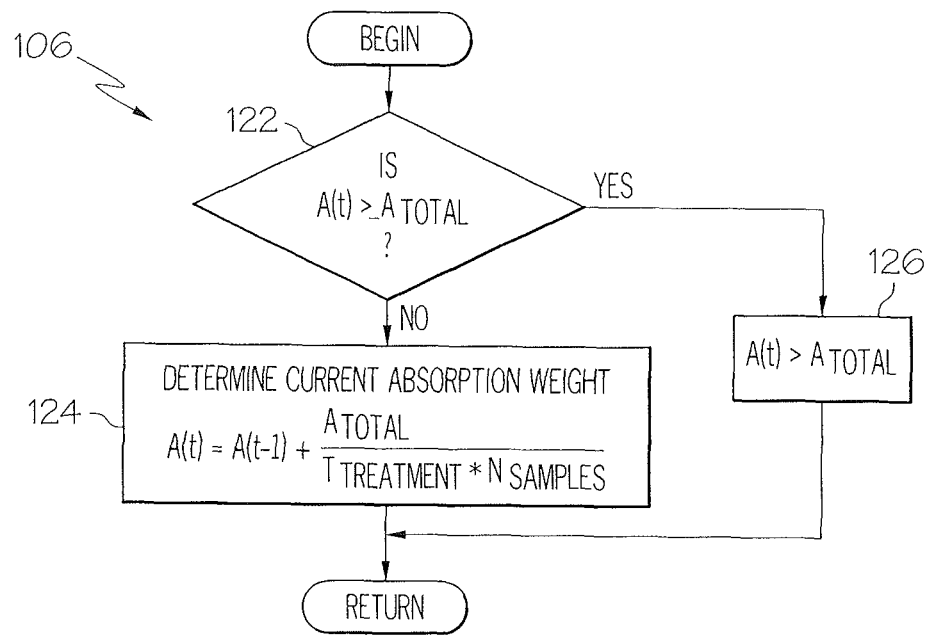
FIG. 6 is a detailed flow diagram of an operation for performing the step of computing the current absorption weight of the sorbent cartridge, in accordance with embodiments of the present invention.

FIG. 6 is a detailed flow diagram of an operation for performing the step 106 of computing the current absorption weight of the sorbent cartridge, in accordance with embodiments of the present invention. As described above, in addition to the dynamic compliant behavior exhibited by the sorbent cartridge 30 described above, the sorbent cartridge further 30 exhibits an absorption behavior. During a dialysis procedure, the sorbent cartridge 30 stores more dialysate as the time of the procedure increases. Referring to FIG. 4 above, based on a linear model for sorbent cartridge absorption, the current absorption weight A(t) is determined as:

$$A(t)=A(t-1)+(A_{total}/(t_{treatment}*N_{samples})) \quad (3)$$

In this relationship: A(t) represents the current absorption weight; A(t−1) is the first part of the equation and represents the previously computed current absorption weight, that is, computed at the last iteration of the operation; $A_{total}$ represents a predetermined total absorption weight capacity of the sorbent cartridge; $t_{treatment}$ represents the total treatment time and $N_{samples}$ represents the number of samples per unit of treatment time. In an example where the total treatment time is four hours and the sample rate is 4 samples per second, then $t_{treatment}$ is (240 minutes*60 seconds/minute=14400 seconds) and $N_{samples}$ is 4. In this example, assuming the maximum total absorption weight of the sorbent cartridge to be determined as 125 ml, then, for each sample, the absorption weight A(t) will be increased by (125 ml/((14400*4) samples)), or 0.00217 ml/sample.

Referring to the flow diagram of FIG. 6, at step 122, it is first determined whether the current absorption weight A(t) is greater than or equal to the predetermined total absorption weight capacity of the sorbent cartridge $A_{total}$. In the event that the current absorption weight A(t) is greater than or equal to the predetermined total absorption weight capacity of the sorbent cartridge $A_{total}$, then the current absorption weight A(t) is set to equal the predetermined total absorption weight capacity of the sorbent cartridge $A_{total}$, at step 126.

In the event that the current absorption weight A(t) is greater than or equal to the predetermined total absorption weight capacity of the sorbent cartridge $A_{total}$, then the current absorption weight A(t) is determined according to the relationship described above at equation (3), at step 124.

Figure 7:
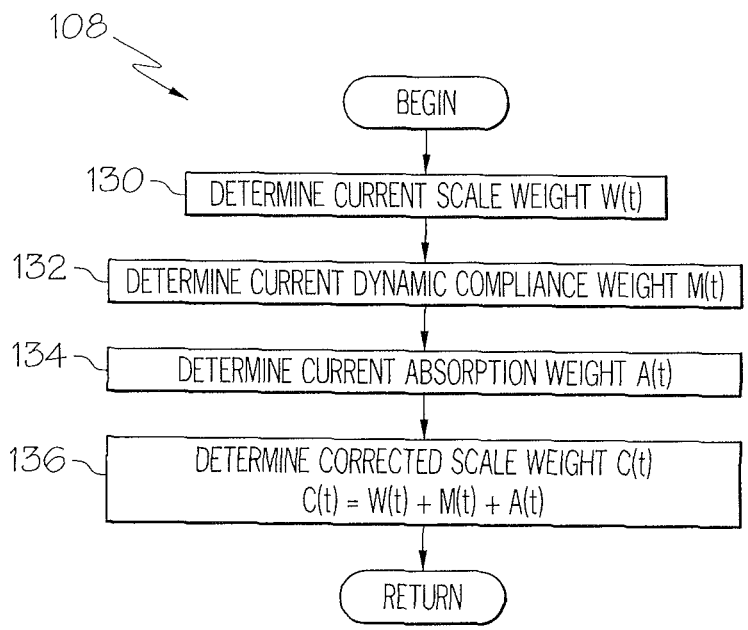
FIG. 7 is a detailed flow diagram of an operation for performing the step of computing a corrected scale weight, in accordance with embodiments of the present invention.

FIG. 7 is a detailed flow diagram of an operation for performing the step 108 of computing a corrected scale weight C(t), in accordance with embodiments of the present invention. As described above, the compensation system 120 adjusts the sampled weight signal 44 sampled at step 102 by the dynamic compliance computed at step 104 and by the absorption level calculated at step 106. In this embodiment, the current scale weight W(t) is determined at step 130 (see step 102 of FIG. 3 above); the current dynamic compliance weight M(t) is determined at step 132 (see step 104 of FIG. 3 above); and the current absorption weight A(t) is determined at step 134 (see step 106 of FIG. 3 above).

A corrected scale weight C(t) is computed as a result of the adjustment at step 136 (see step 108 of FIG. 3 above):

$$C(t)=W(t)+M(t)+A(t) \quad (4)$$

where: W(t) represents the current sampling of the weight signal 44; M(t) represents the current dynamic compliance weight; and A(t) represents the current absorption weight.

Figure 8:
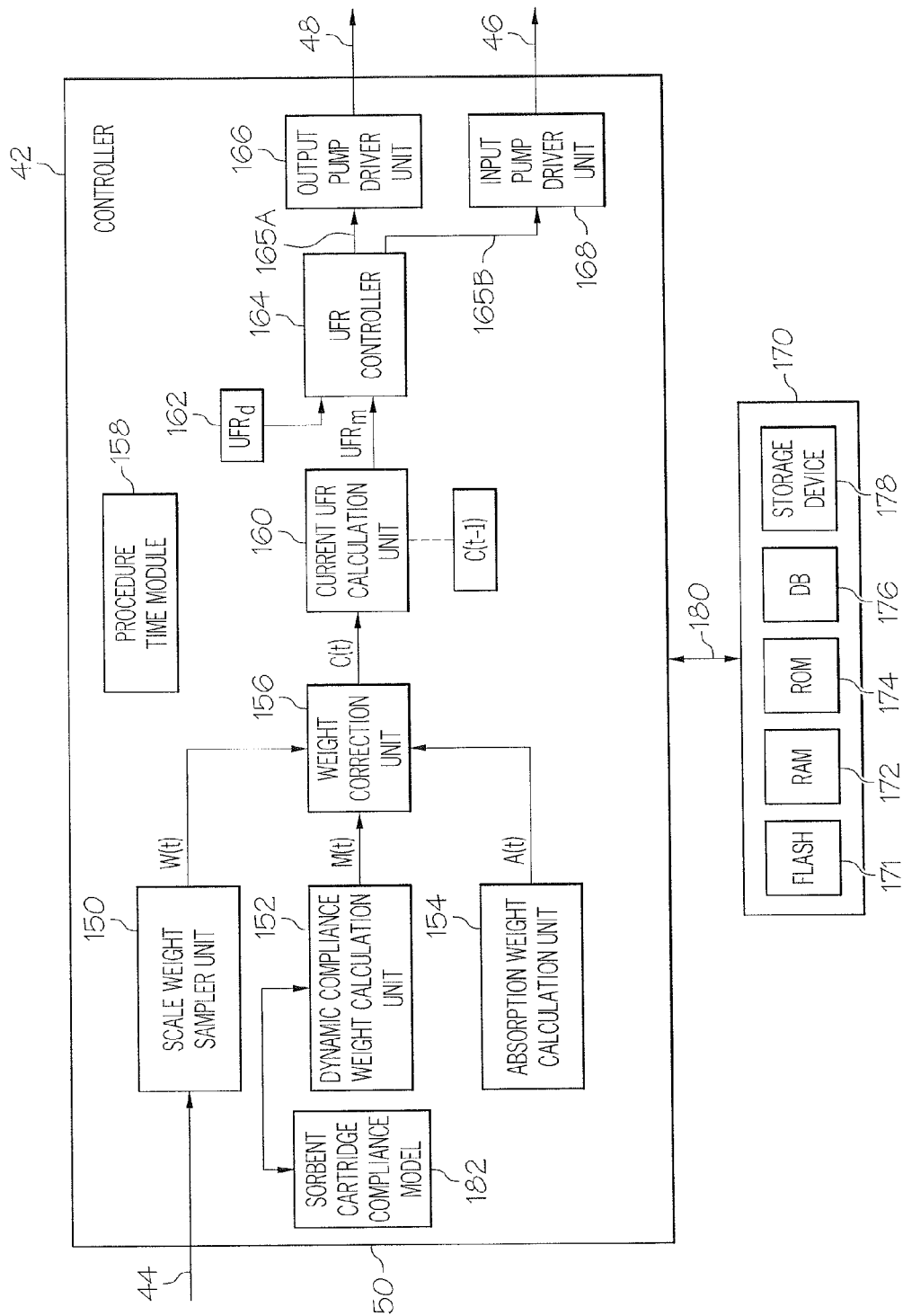
FIG. 8 is a detailed block diagram of an example embodiment of the controller, in accordance with embodiments of the present invention.

FIG. 8 is a detailed block diagram of an example embodiment of the controller 42 of FIG. 1. The controller 42 includes a plurality of computation units that can be implemented in any of a number of different configurations, depending on the architecture desired. For example the computation units can comprise software modules that operate on, or in connection with, a processor, as well as firmware, or digital or analog hardware.

In the present example embodiment, the controller 42 comprises a procedure time module 158, a scale weight sampler unit 150, a dynamic compliance weight calculation unit 152, a sorbent cartridge compliance model 182, an absorption weight calculation unit 154, a weight correction unit 156, a current ultrafiltration rate calculation unit 160, an ultrafiltration rate controller 164, an output pump driver unit 166 and an input pump driver unit 168.

The procedure time module 158 records the elapsed time t of the procedure and makes that elapsed time t value available to any modules or units operating in connection with the controller 42. The procedure time module 158 can also track the amount of time elapsed between contiguous scale samples, or any other time calculations required by the controller 42.

The scale weight sampler unit 150 samples the weight signal 44 to provide a current sampled weight signal W(t), for example in the manner described above in connection with step 102 of FIG. 3.

The dynamic compliance weight calculation unit 152 calculates the current dynamic compliance weight M(t), for example in the manner described above in connection with step 104 of FIGS. 3 and 5. The sorbent cartridge compliance model 182 can be accessed by the dynamic compliance weight calculation unit 152, as described above.

The absorption weight calculation unit 154 calculates the current absorption weight A(t), for example in the manner described above in connection with step 106 of FIGS. 3 and 6.

The weight correction unit 156 receives the current sampled weight signal W(t), the current dynamic compliance weight M(t), and the current absorption weight A(t), and computes the corrected scale weight C(t), for example in the manner described above in connection with step 108 of FIGS. 3 and 7. In one example embodiment, the weight correction unit 156 comprises an adder or a summation module.

The current ultrafiltration rate calculation unit 160 receives the corrected scale weight signal C(t), and calculates an updated measured ultrafiltration rate $UFR_m$. In one embodiment, the updated measured ultrafiltration rate $UFR_m$ is calculated as a function of the difference between the current corrected scale weight C(t) and a previous corrected scale weight C(t−1), divided by the elapsed time since the last sample $t_s$.

$$UFR_m=(C(t)-C(t-1))/t_s, \quad (5)$$

for example in the manner described above.

The ultrafiltration rate controller 164 receives the updated measured ultrafiltration rate $UFR_m$ and determines whether adjustments to the system ultrafiltration rate are needed. As described above, in one example embodiment, this operation is performed by a proportional integral derivative controller (PID) that periodically monitors the measured ultrafiltration rate $UFR_m$ and compares that to a desired ultrafiltration rate $UFR_d$. In one example embodiment, the desired ultrafiltration rate $UFR_d$ is prescribed by a physician, and typically, this value ranges between 0.75 liters/hour to 2 liters/hour. In one example embodiment, the desired ultrafiltration rate $UFR_d$ is stored in a register 162, or other storage medium such as memory that is available to the controller 42. In the event that the PID determines that an adjustment to the ultrafiltration rate of the procedure is needed, then the output signals 165A, 165B to the output pump driver unit 166 and/or the input pump driver unit 168 are controlled to modify the ultrafiltration rate.

The output pump driver unit 166 and the input pump driver unit 168 receive control signals 165A, 165B from the ultrafiltration rate controller 164 and respectively provide the output rate signal 48 to the output pump 38 and the input rate signal 46 to the input pump 36.

In various embodiments, the controller 42 can comprise a single processor, for example, a central processing unit (CPU), that stores and retrieves data from an electronic information (e.g., data) storage system 170 via a data bus 180. As will be appreciated by those skilled in the art, while the controller 42 is shown with a specific set of components, units or modules, embodiments applicable to the present invention are not limited thereto. It is understood that the type, number and connections among and between the listed components, units or modules are exemplary only and are not intended to be limiting.

In the illustrative embodiment, the controller 42 can be implemented as a CPU, which may include any of a variety of types of processors known in the art (or developed hereafter), such as a general purpose microprocessor, a digital signal processor or a microcontroller, or a combination thereof. The CPU may be operably coupled to storage systems 170 and configured to execute sequences of computer program instructions to perform various processes and functions associated with the operations described herein. The computer program instructions may be loaded into any one or more of the storage media depicted in storage system 170 or in other locations.

The storage system 170 can include any of a variety of semiconductor memory devices, such as, for example, random-access memory (RAM) 172, read-only memory (ROM) 174, flash memory 171, or other memory card (not shown). The storage system 170 can further include at least one database 176, at least one storage device or system 178, or a combination thereof. The storage device 178 can include any type of mass storage media configured to store information and instructions that the controller 42 may require to perform the various processes and functions described herein. As examples, the data storage device 178 may include a disk storage system or a tape storage system. A disk storage system may include an optical or magnetic storage media, including, but not limited to, a floppy drive, a zip drive, a hard drive, a "thumb" drive, a read/write CD ROM or other type of storage system or device. A tape storage system may include a magnetic tape, or other type of tape system.

It should be noted that although not shown in the diagram of FIG. 8, the infusate material added to the fresh dialysate output by the sorbent cartridge 30 from the infusate reservoir 60 (see FIG. 1 above), has a certain weight that needs to be compensated for over the time of the procedure. In certain embodiments, the infusate weight is monitored by a scale that measures the weight of the infusate reservoir 60. The infusate weight is gradually proportioned into the system, for example, at a rate of 1/342 times the dialysate flow rate. The infusate is proportioned into the dialysate because the sorbent cartridge extracts cations (Ca++, Mg++, and K++) from the dialysate. The infusate concentration is established by prescription, and is proportioned into the dialysate to osmotically balance the cation electrolytes in the patient. When the dialysate matches the patient, electrolytes no osmotic transfer from the patient into the dialysate occurs in the dialyzer. When the dialysate passes through the cartridge, after the dialyzer exchange, the cartridge removes the ionic content. In view of this, the infusate is continuously infused while the dialysate is flowing to keep the electrolytes in the patient. In one embodiment, the infusate can be proportioned by the controller 42, or by another dedicated controller, based on the dialysate flow rate of the procedure and based on the weight of the infusate reservoir on the scale.

Figure 9:
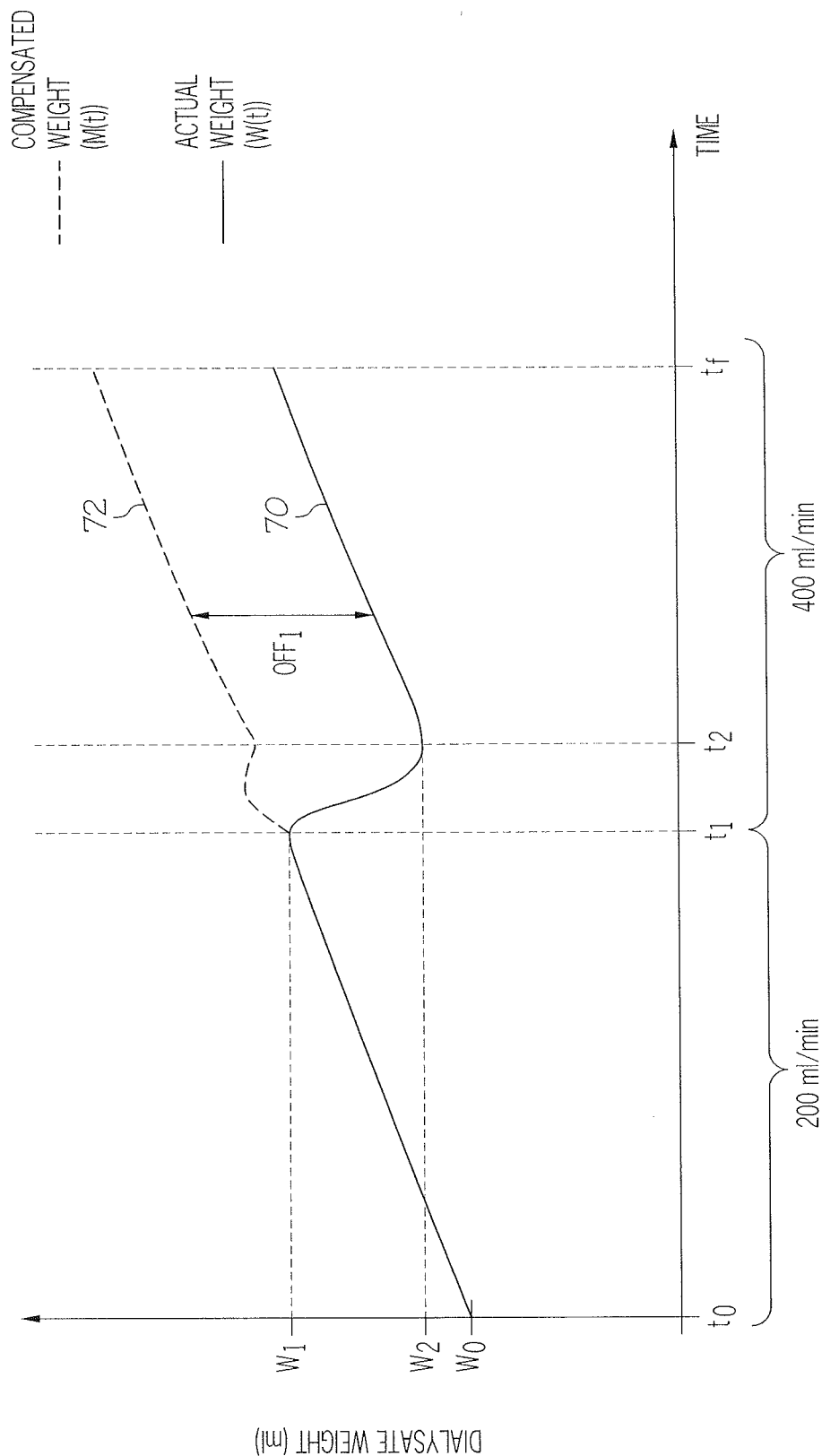
FIG. 9 is a graph illustrating a result of a tracking of a weight signal output by the scale from an initial time $t_0$ to a final time $t_f$ in a first part of a representative treatment.
Figure 10:
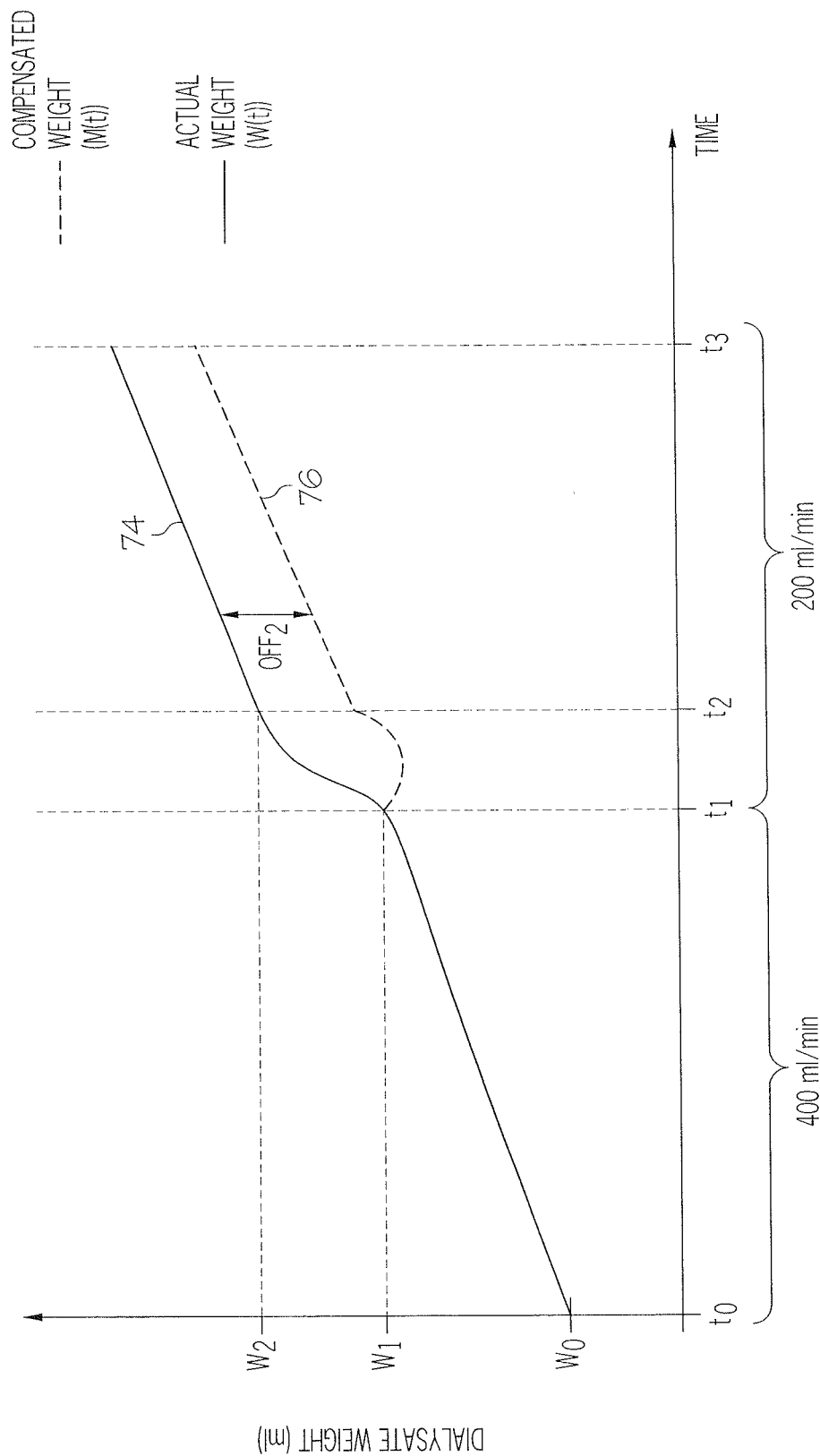
FIG. 10 is a graph illustrating a result of a tracking of a weight signal output by the scale from an initial time $t_0$ to a final time $t_f$ in a second part of the representative treatment.

The graphs of FIGS. 9 and 10 are representative of the compliant behavior of a sorbent cartridge. The representative data assumes that a regenerative dialysis system of the type illustrated in FIG. 1 and employing a sorbent cartridge 30, such as the "Hi-sorb R-3500" sorbent cartridge made by Sorb Technology, Oklahoma City, Okla., a wholly owned subsidiary of Fresenius Medical Care North America, Waltham, Mass., is placed in treatment. The blood flow rate through the dialyzer is selected to be a typical rate of 500 ml/min.

In a first part of the representative treatment, the dialysate flow rate of the regenerative dialysis system is selected to be a typical rate of 200 ml/min. As described above, the dialysate flow rate is determined as the input flow rate of the input pump 36. The actual scale weight of the dialysate contained in the dialysate reservoir 32 was measured by a scale 34 and the resulting weight signal was tracked from an initial time $t_0$ to a final time $t_f$.

FIG. 9 is a graph illustrating the result of the tracking of the weight signal 44 output by the scale 34 from the initial time $t_0$ to a final time $t_f$ in the first part of the representative treatment.

At the initial time $t_0$, an initial dialysate weight W0 is measured by the scale 34. The initial weight W0 is representative of the initial volume of dialysate present in the dialysate reservoir 32 at the initial time $t_0$. Between the initial time $t_0$ and a final time $t_f$, the dialysate flow rate was controlled to be the typical rate of 200 ml/min. In one example, the input flow rate of the input pump was thus set to 200 ml/min and the output flow rate of the output pump was thus set to 210 ml/min to ensure a positive ultrafiltration rate of 10 ml/min. The positive slope of the measured weight signal graph 70 between the initial time $t_0$ and the first time $t_1$ indicates an increase in the volume of the dialysate stored in the dialysate reservoir 32 as a result of a positive ultrafiltration rate during the procedure. This indicates that fluid was being pulled from the patient through the dialyzer 20 during the procedure.

At the first time $t_1$, the dialysate flow rate of the system was changed from the typical rate of 200 ml/min to another typical rate of 400 ml/min. The input flow rate of the input pump 36 was thus changed from 200 ml/min to 400 ml/min and the output flow rate of the output pump 38 was accordingly changed from 210 ml/min to 410 ml/min in order to maintain the positive ultrafiltration rate of 10 ml/min. At this first time $t_1$, the weight of the dialysate as measured by the scale was a first weight W1.

As a result of the change in the dialysate flow rate from 200 ml/min to 400 ml/min at the first time $t_1$, it can be seen that an immediate drop in the measured weight signal of the dialysate in the dialysate reservoir 32 occurred between the time period between the first time $t_1$ and a second time $t_2$ from the first weight W1 to a second weight W2 respectively. The weight of the dialysate in the dialysate reservoir did drop during this time period from the first weight W1 to a second weight W2, so the measured weight signal is accurate; however, fluid was not transported back to the patient. Instead, as described above, fluid is displaced from the dialysate reservoir 32 to the sorbent cartridge 30 during this time period, due to the compliant behavior exhibited by the sorbent cartridge 30 as a result of the increase in the dialysate flow rate from 200 ml/min to 400 ml/min. Between the second time $t_2$ and the final time $t_f$, the dialysate flow rate was maintained at 400 ml/min, and the sorbent cartridge continues to store the displaced additional fluid, due to its compliant behavior, as a result of the increased dialysate flow rate. The positive slope of the graph between the second time $t_2$ and the final time $t_f$ indicates an increase in the volume of the dialysate stored in the dialysate reservoir 32 as a result of a positive ultrafiltration rate during this period of the procedure. This indicates that fluid was being pulled from the patient through the dialyzer 20 during this period of the procedure.

Between the first time $t_1$ and the second time $t_2$, absent any corrective or compensatory measures, the controller 42 could determine the reduced weight measurement from the first weight W1 to a second weight W2 as an indication that the ultrafiltration rate should be increased, since, relative to the first time $t_1$, it would appear that the system is not keeping pace with the desired ultrafiltration rate. Similarly, between the second time $t_2$ and the final time $t_f$, absent any corrective or compensatory measures, the controller 42 could make a similar, improper determination.

In a second part of the representative treatment, the dialysate flow rate of the regenerative dialysis system is selected to be a typical rate of 400 ml/min. As described above, the dialysate flow rate is determined as the input flow rate of the input pump 36. The actual scale weight of the dialysate contained in the dialysate reservoir 32 was measured by a scale 34 and the resulting weight signal was tracked from an initial time $t_0$ to a final time $t_f$.

FIG. 10 is a graph illustrating the result of the tracking of the weight signal 44 output by the scale 34 from the initial time $t_0$ to a final time $t_f$ in the second part of the representative treatment.

At the initial time $t_0$, an initial dialysate weight W0 is measured by the scale 34. The initial weight W0 is representative of the initial volume of dialysate present in the dialysate reservoir 32 at the initial time $t_0$. Between the initial time $t_0$ and a final time $t_f$, the dialysate flow rate was controlled to be the typical rate of 400 ml/min. In one example, the input flow rate of the input pump was thus set to 400 ml/min and the output flow rate of the output pump was thus set to 410 ml/min to ensure a positive ultrafiltration rate of 10 ml/min. The positive slope of the measured weight signal graph 74 between the initial time to and the first time $t_1$ indicates an increase in the volume of the dialysate stored in the dialysate reservoir 32 as a result of a positive ultrafiltration rate during the procedure. This indicates that fluid was being pulled from the patient through the dialyzer 20 during the procedure.

At the first time $t_1$, the dialysate flow rate of the system was changed from the typical rate of 400 ml/min to another typical rate of 200 ml/min. The input flow rate of the input pump 36 was thus changed from 400 ml/min to 200 ml/min and the output flow rate of the output pump 38 was accordingly changed from 410 ml/min to 210 ml/min. in order to maintain the positive ultrafiltration rate of 10 ml/min. At this first time $t_1$, the weight of the dialysate as measured by the scale was a first weight W1.

As a result of the change in the dialysate flow rate from 400 ml/min to 200 ml/min at the first time $t_1$, it can be seen that an immediate rise in the measured weight signal 74 of the dialysate in the dialysate reservoir 32 occurred between the time period between the first time $t_1$ and a second time $t_2$ from the first weight W1 to a second weight W2 respectively. The weight of the dialysate in the dialysate reservoir did increase during this time period from the first weight W1 to a second weight W2, so the measured weight signal is accurate; however, an increased amount of fluid was not drawn from the patient during that time period. Instead, as described above, fluid is being displaced from the sorbent cartridge 30 to the dialysate reservoir 32 during this time period, due to the compliant behavior exhibited by the sorbent cartridge 30 as a result of the decrease in the dialysate flow rate from 400 ml/min to 200 ml/min. Between the second time $t_2$ and the final time $t_f$, the dialysate flow rate was maintained at 200 ml/min, and the displaced fluid remains in the dialysate reservoir 32, due to the compliant behavior of the sorbent cartridge 30, as a result of the decreased dialysate flow rate. The positive slope of the graph between the second time $t_2$ and the final time $t_f$ indicates an increase in the volume of the dialysate stored in the dialysate reservoir 32 as a result of a positive ultrafiltration rate during this period of the procedure. This indicates that fluid was being pulled from the patient through the dialyzer 20 during this period of the procedure.

Between the first time $t_1$ and the second time $t_2$, absent any corrective or compensatory measures, the controller 42 could determine the increased weight measurement from the first weight W1 to a second weight W2 as an indication that the ultrafiltration rate should be decreased, since, relative to the first time $t_1$, it would appear that the system is exceeding the desired ultrafiltration rate. Similarly, between the second time $t_2$ and the final time $t_f$, absent any corrective or compensatory measures, the controller could make a similar, improper determination.

During the above-described representative treatment, the controller 42 was programmed to compensate for the compliant behavior exhibited by the sorbent cartridge of the regenerative dialysis system. Referring back to FIG. 9, a second graph provides an representative compensation weight signal 72 that was automatically calculated by the controller 42 based on the measured weight signal 44. The resulting compensated weight signal 72 reflected the dialysate fluid present in the dialysate reservoir 32 as measured by the scale 34, as well as any additional dialysate fluid calculated to be present in the sorbent cartridge 30 during the experimental procedure.

It can be seen in FIG. 9 that between the initial time $t_0$ and the first time $t_1$, the compensated weight signal 72 tracked the measured weight signal 70. Following this, between the first time $t_1$ and the second time $t_2$, the actual weight signal 70 is progressively reduced as a result of the progression of displacement of dialysate from the dialysate reservoir 32 to the sorbent cartridge 30, due to the increase in dialysate flow rate from 200 ml/min to 400 ml/min, as described above. Beginning at the first time $t_1$, the controller 42 changes the compensation amount to reflect a transition to the new dialysate flow rate. It can be seen that during the brief period between the first time $t_1$ and the second time $t_2$, the compensated weight signal 72 briefly undergoes an upward excursion, then settles into an expected level. This is due to an imperfection in the modeling of the compliant behavior of the sorbent cartridge. However, the upward excursion is insignificant, and represents a temporary increase on the order of about 1-2% of the desired compensated weight measurement 72. Following the transition time period between the first time $t_1$ and the second time $t_2$, the compensated weight signal 72 returns to a linear, upward trend that is representative of a positive ultrafiltration rate.

It should be noted that the actual weight W(t) signal 70 exhibits non-linear behavior between the first time $t_1$ and the second time $t_2$. Such non-linear behavior is attributable to the fluidic capacitive and fluidic inductive compliant behavior of the sorbent cartridge 30 during the period of time following the change in dialysate flow rate at the first time $t_1$. The upward excursion in the compensated weight signal M(t) signal 72 during this time can be further corrected by applying a non-linear second-order or third order model to correct for the non-linear compliant behavior of the cartridge. Depending on the level of precision required, however, it may be determined that a first-order model resulting in a minor upward excursion is sufficient.

The slopes of the linear portions of the compensated weight signal 72 between the initial time $t_0$ and the first time $t_1$, and between the second time $t_2$ and the final time $t_f$ are generally equal, illustrating that the output pump rate of the output pump 38 was correspondingly adjusted at the time $t_1$ of the transition to maintain the same ultrafiltration rate prior to and subsequent to the transition; thus, the same ultrafiltration rate was maintained at the respective different dialysate flow rates of 200 ml/min and 400 ml/min. In contrast, while the slopes of the linear portions of the actual weight signal 70 between the initial time $t_0$ and the first time $t_1$, and between the second time $t_2$ and the final time $t_f$ are generally equal, their weight values are offset in the y-axis of the graph to correspond with the fluid displaced from the dialysate fluid reservoir 32 to the sorbent cartridge 30 as a result of the increased dialysate flow rate.

The first offset $Off_1$ between the actual measured weight 70 and the compensated weight 72 between the second time $t_2$ and the final time $t_f$ is substantially constant and is representative of the difference between the compensated weight M(t) and the actual measured weight W(t), which is the amount of dialysate that is displaced to the sorbent cartridge 30 as a result of the increase in dialysate flow rate from 200 ml/min to 400 ml/min It can be seen from the graph of FIG. 9 that the compensated weight signal 72 much more closely reflects the amount of fluid that has been drawn from the patient between the initial time $t_0$ and the final time $t_f$. In particular, the compensated weight signal 72 compensates for compliant behavior in the sorbent cartridge 30, and in other system components that may behave compliantly. In an embodiment of the invention, the compensated weight signal 72 is used by the controller 42 to perform further automated adjustments to the input rate signal 46 and to the output rate signal 48 to respectively adjust the input pump 36 and the output pump 38 so as to control the ultrafiltration rate of the dialysis procedure in a manner that is safe, accurate and effective for the patient.

Referring again to FIG. 10, the second graph of this figure similarly provides a representative compensation weight signal 76 that was automatically calculated by the controller 42 based on the collected weight signal 44. The resulting compensated weight signal 76 reflected the dialysate fluid present in the dialysate reservoir 32 as measured by the scale 34, as well as any additional dialysate fluid calculated to be present in the sorbent cartridge 30 during the experimental procedure.

It can be seen in FIG. 10 that between the initial time $t_0$ and the first time $t_1$, the compensated weight signal 76 tracked the measured weight signal 74. Following this, between the first time $t_1$ and the second time $t_2$, the actual weight signal 74 is progressively increased as a result of the progression of displacement of dialysate from the sorbent cartridge 30 to the dialysate reservoir 32, due to the decrease in dialysate flow rate from 400 ml/min to 200 ml/min, as described above. Beginning at the first time $t_1$, the controller 42 changes the compensation amount to reflect a transition to the new dialysate flow rate. It can be seen that during the brief period between the first time $t_1$ and the second time $t_2$, the compensated weight signal 76 briefly undergoes a downward excursion, then settles into an expected level. In a manner similar to the representative treatment given above in connection with FIG. 9, this is due to an imperfection in the modeling of the compliant behavior of the sorbent cartridge. However, the downward excursion is insignificant, and represents a temporary decrease on the order of about 1-2% of the desired compensated weight measurement 76. Following the transition time period between the first time $t_1$ and the second time $t_2$, the compensated weight signal 76 returns to a linear, upward trend that is representative of the normal, desired positive ultrafiltration rate.

As in FIG. 9, it should be noted that in the representative data of FIG. 10 the actual weight W(t) signal 74 exhibits non-linear behavior between the first time $t_1$ and the second time $t_2$. Such non-linear behavior is attributable to the fluidic capacitive and fluidic inductive compliant behavior of the sorbent cartridge 30 during the period of time following the change in dialysate flow rate at the first time $t_1$. The downward excursion in the compensated weight signal M(t) signal 76 during this time can be further corrected by applying a non-linear second-order or third order model to correct for the non-linear compliant behavior of the cartridge. Depending on the level of precision required, however, it may be determined that a first-order model resulting in a minor downward excursion is sufficient.

The slopes of the linear portions of the compensated weight signal 76 between the initial time $t_0$ and the first time $t_1$, and between the second time $t_2$ and the final time $t_f$ are generally equal, illustrating that the output pump rate of the output pump 38 was correspondingly adjusted at the time $t_1$ of the transition to maintain the same ultrafiltration rate prior to and subsequent to the transition; thus, the same ultrafiltration rate was maintained at the respective different dialysate flow rates of 400 ml/min and 200 ml/min. In contrast, while the slopes of the linear portions of the actual weight signal 74 between the initial time $t_0$ and the first time $t_1$, and between the second time $t_2$ and the final time $t_f$ are generally equal, their weight values are offset in the direction of the y-axis of the graph to correspond with the fluid displaced from the sorbent cartridge 30 to the dialysate fluid reservoir 32 as a result of the increased dialysate flow rate.

The second offset $Off_2$ between the actual measured weight 74 and compensated weight 76 between the second time $t_2$ and the final time $t_f$ is substantially constant and is representative of the difference between the compensated weight M(t) and the actual measured weight W(t), which is the amount of dialysate that is displaced to the reservoir cartridge 32 as a result of the decrease in dialysate flow rate from 400 ml/min to 200 ml/min.

It can be seen from the graph of FIG. 10 that the compensated weight signal 76 much more closely reflects the amount of fluid that has been drawn from the patient between the initial time $t_0$ and the final time $t_f$. In particular, the compensated weight signal 76 compensates for compliant behavior in the sorbent cartridge 30, and in other system components that may behave compliantly. In an embodiment of the invention, the compensated weight signal 76 is used by the controller 42 to perform further automated adjustments to the input rate signal 46 and to the output rate signal 48 to respectively adjust the input pump 36 and the output pump 38 so as to control the ultrafiltration rate of the dialysis procedure in a manner that is safe, accurate and effective for the patient.

Referring again to FIG. 1, the sorbent cartridge 30 can comprise a housing containing a sorbent cartridge capable of removing uremic toxins. In some embodiments, the cartridge is disposable. The cartridge can, for example, be constructed such that it can be disposed after use and removed from the housing. The replaced cartridge could then be replaced with a similar cartridge for a subsequent use of the system 28. The cartridge can purify water and regenerate spent dialysis solution through the use of a series of layers which can remove heavy metals (e.g., lead, mercury, arsenic, cadmium, chromium and thallium), oxidants (e.g., chlorine and chloramine), urea, phosphate and other uremic waste metabolites (e.g., creatinine and uric acid) from the solution, without removing or adsorbing excessive amounts of cations (e.g., calcium, magnesium, sodium, potassium) or essential ions.

In some embodiments, the components of the sorbent cartridge that perform the aforementioned functions include a purification layer that includes activated carbon; an ion exchange layer that includes a polymer phosphate binder or an ion exchange sorbent; and a urea removal layer that includes strong acid cation exchange resin and basic resin(s) or urea-degrading enzymes and an ion exchange sorbent together with a composition that rejects cations (e.g., flat membrane/hollow fibers described further herein, an ion-exchange membrane, or an encapsulation surrounding the urea removal components).

In certain embodiments, the sorbent cartridge includes the following layers and materials: sodium zirconium carbonate or other alkali metal-Group IV metal-carbonate; zirconium phosphate or other ammonia adsorbents; alumina or other like material; alumina supported urease or other immobilized enzyme layer or other material to convert urea to ammonia, such as diatomaceous earth or zirconium oxide; and granular activated carbon, such as charcoal, or other adsorbent. The sodium zirconium carbonate component can act as a phosphate adsorbent. The zirconium oxide can be capable of acting as a counter ion or ion exchanger to remove phosphate, and can be in the form of hydrous zirconium oxide (e.g., hydrous zirconium oxide containing acetate). The zirconium oxide can also be blended with the sodium zirconium carbonate when positioned in the cartridge.

Non-limiting examples of urea-degrading enzymes that can be employed in either embodiment of the sorbent cartridge include enzymes that are naturally occurring (e.g. urease from jack beans, other seeds or bacteria), produced by recombinant technology (e.g., in bacterial, fungal, insect or mammalian cells that express and/or secrete urea-degrading enzymes) or produced synthetically (e.g., synthesized). In some embodiments, the enzyme is urease.

In certain embodiments, the sorbent cartridge further includes hollow fibers. The hollow fibers can reject positively charged ions, as well as increase the capacity of the cartridge. The hollow fibers can be coated with an ion-rejecting material, which through a water-purification like mechanism allows the urea through but rejects positively charged ions such as calcium and magnesium. The material coating the hollow fibers can be any such material known to one of skill in the art (e.g., fatty acids or polymer chains like polysulfone) that can effectively reject calcium and magnesium and therefore retain the ions in the dialysis solution. Generally, to have this effect the material itself would be positively charged. In some embodiments, for example, the material used to coat the hollow fibers is cellulose acetate (e.g., cellulose triacetate). The hollow fibers that are to be coated are commercially available (e.g., Fresenius Medical Care North America) and can be coated with any desired ion-rejecting material available to one having skill in the art.

Alternatively, the hollow fibers can include an ion-selective nanofiltration membrane. Such membranes are commercially available from a number of sources (e.g., Amerida, Koch, GE, Hoechst and Dow Chemical). These membranes have pore sizes that prevent ionic substances from diffusing through the membrane. For example, there are nanofiltration membranes that have an ability to reject ions with more than one negative charge (e.g., sulfate and phosphate) while allowing single-charged ions to pass through, with the converse also being the case. In either case, the hollow fiber devices are available in a variety of dimensions and need only be small enough to fit in the replaceable cartridge, which can be sized for use in an in-home system.

In certain embodiments, the sorbent cartridge can further include a flat membrane that is covered with a positively charged material like those described above. In addition, the membrane can be an ion exchange (e.g., anion) membrane that limits the passage of positively charged ions (e.g., Astrom® Neosepta® AFX anion exchange membrane, PCA GmbH PC-SA anion exchange membrane). Advantageously, this ion exchange membrane also has an ability to adsorb phosphate.

The cartridge and/or its components or layers can be replaced (e.g., membrane, urea-degrading enzyme), regenerated (e.g., resin, sorbent) and/or sterilized for re-use when necessary (e.g., saturation, damage, depletion). In addition, the entire cartridge can be replaceable and thus removed from the dialysis system when there is a decrease in the regeneration efficiency of the cartridge (e.g., through layer saturation) or the cartridge becomes worn or damaged, for instance.

Further examples of sorbent cartridges are described in U.S. Pat. No. 6,878,283; U.S. Pat. No. 7,033,498; in the REDY cartridge, available from Sorb Technology, Oklahoma City, Okla., a wholly owned subsidiary of Fresenius Medical Care North America, Waltham, Mass.; and in "Sorbent Dialysis Primer" COBE Renal Care, Inc. Sep. 4, 1993 Edition, and "Rx Guide to Custom Dialysis" COBE Renal Care Inc. Revision E. September 1993, all incorporated in their entirety by reference herein.

Other units in the system of FIG. 1 can behave compliantly, including the tubes connecting the various units, various pressure transducers and other hydraulic components of the system, including temperature sensors, pressure sensors, optical ammonia sensors, ultrasonic flow sensors, air bubble detectors, the heparin pump and the infusate pump. In current systems, hydraulic pressure transducers exhibiting compliant behavior can be employed as a safety mechanism to prevent excessive pressure spikes. When an out-of-bounds pressure condition is determined, the procedure can be halted, and visual or audio alarm can be activated.

However, relative to the amount of compliance exhibited by the sorbent cartridge 30, and relative to the volume of fluid contained in the sorbent cartridge 30, the compliant behavior of other components in the system amounts to only a small percentage of displaced dialysate fluid, for example, on the order of fractions of milliliters, generally amounting to at least an order of magnitude lower than the compliance exhibited by the sorbent cartridge. Embodiments of the present invention are equally effective in compensating for compliance behavior in these other units.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A regenerative dialysis system, comprising:
an input pump that pumps fresh dialysate fluid into a dialyzer at an input rate;
an output pump that pumps used dialysate fluid from the dialyzer at an output rate, an ultrafiltration rate of the system being related to the output rate relative to the input rate;
a sorbent cartridge that filters the used dialysate fluid to generate the fresh dialysate fluid; and a controller that controls the ultrafiltration rate of the system in response to a compliance model of the sorbent cartridge that provides a predefined model of compliant behavior related to the sorbent cartridge that is based on a relationship between a volume of dialysate fluid stored by the sorbent cartridge as a function of a flow rate of the dialysate fluid through the sorbent cartridge.

2. The system of claim 1 wherein the system further comprises:
a reservoir that stores the fresh dialysate fluid;
a scale that monitors the scale weight of the fresh dialysate fluid stored in the reservoir; and
wherein the controller further controls the ultrafiltration rate in response to the scale weight of the fresh dialysate fluid in the reservoir.

3. The system of claim 2 wherein the controller further:
calculates a dynamic weight of dialysate fluid stored in the sorbent cartridge in response to the flow rate of the dialysate fluid through the sorbent cartridge;
calculates a corrected dialysate fluid weight by summing the dynamic weight and the scale weight; and
controls the ultrafiltration rate of the system in response to the corrected dialysate fluid weight.

4. The system of claim 3 wherein the controller calculates the dynamic weight of the dialysate fluid over a time period of a treatment procedure.

5. The system of claim 3 wherein the controller further:
calculates an absorption weight of dialysate fluid stored in the sorbent cartridge as a result of time-based absorption; and
calculates the corrected dialysate fluid rate by further summing the absorption weight with the dynamic weight and the scale weight.

6. The system of claim 1 wherein the relationship between the volume of dialysate fluid stored by the sorbent cartridge as a function of flow rate of the dialysate fluid through the sorbent cartridge is linear.

7. The system of claim 1 wherein the relationship between the volume of dialysate fluid stored by the sorbent cartridge as a function of flow rate of the dialysate fluid through the sorbent cartridge is non-linear.

8. The system of claim 1 wherein the ultrafiltration rate is a rate at which fluid is removed from a patient at the dialyzer.

9. The system of claim 1 wherein the ultrafiltration rate of a dialysis procedure performed by the regenerative dialysis system is prescribed.

10. A method of controlling ultrafiltration rate of a regenerative dialysis system, comprising:
pumping fresh dialysate fluid into a dialyzer at an input rate;
pumping used dialysate fluid from the dialyzer at an output rate, an ultrafiltration rate of the regenerative dialysis system being related to the output rate relative to the input rate;
filtering the used dialysate fluid to generate the fresh dialysate fluid at a sorbent cartridge; and
controlling the ultrafiltration rate of the regenerative dialysis system in response to a compliance model of the sorbent cartridge that provides a predefined model of compliant behavior related to the sorbent cartridge based on a relationship between a volume of dialysate fluid stored by the sorbent cartridge as a function of a flow rate of the dialysate fluid through the sorbent cartridge.

11. The method of claim 10 further comprising:
storing the fresh dialysate fluid at a reservoir;
monitoring a scale weight of the fresh dialysate fluid stored in the reservoir; and
further controlling the ultrafiltration rate in response to the scale weight of the fresh dialysate fluid in the reservoir.

12. The method of claim 11 further comprising:
calculating a dynamic weight of dialysate fluid stored in the sorbent cartridge in response to the flow rate of the dialysate fluid through the sorbent cartridge; and
calculating the corrected dialysate fluid weight by summing the dynamic weight and the scale weight; and
further controlling the ultrafiltration rate in response to the corrected dialysate fluid weight.

13. The method of claim 12 wherein calculating the dynamic weight of dialysate fluid stored in the sorbent cartridge is performed over a time period of a treatment procedure.

14. The method of claim 12 further comprising:
calculating an absorption weight of dialysate fluid stored in the sorbent cartridge as a result of time-based absorption; and
calculating the corrected dialysate fluid rate by further summing the absorption weight with the dynamic weight and the scale weight.

15. The method of claim 10 wherein the relationship between the volume of dialysate fluid stored by the sorbent cartridge as a function of flow rate of the dialysate fluid through the sorbent cartridge is linear.

16. The method of claim 10 wherein the relationship between the volume of dialysate fluid stored by the sorbent cartridge as a function of flow rate of the dialysate fluid through the sorbent cartridge is non-linear.

17. The method of claim 10 wherein the ultrafiltration rate is a rate at which fluid is removed from a patient at the dialyzer.

18. The method of claim 10 wherein the ultrafiltration rate of a dialysis procedure performed by the regenerative dialysis system is prescribed.

19. A regenerative dialysis system, comprising:
an input pump that pumps fresh dialysate fluid into a dialyzer at an input rate;
an output pump that pumps used dialysate fluid from the dialyzer at an output rate, an ultrafiltration rate of the system being related to the output rate relative to the input rate;
a sorbent cartridge that filters the used dialysate fluid to generate the fresh dialysate fluid;
a controller that controls the ultrafiltration rate of the system in response to a flow rate of the dialysate fluid through the sorbent cartridge, wherein the controller controls the ultrafiltration rate of the system in response to a corrected dialysate fluid weight;
a reservoir that stores the fresh dialysate fluid;
a scale that monitors the scale weight of the fresh dialysate fluid stored in the reservoir, wherein the controller further controls the ultrafiltration rate in response to the scale weight of the fresh dialysate fluid in the reservoir, wherein the controller further:
calculates a dynamic weight of dialysate fluid stored in the sorbent cartridge in response to the flow rate of the dialysate fluid through the sorbent cartridge;
calculates the corrected dialysate fluid weight by summing the dynamic weight and the scale weight;
calculates an absorption weight of dialysate fluid stored in the sorbent cartridge as a result of time-based absorption; and calculates the corrected dialysate fluid rate by further summing the absorption weight with the dynamic weight and the scale weight.

20. A method of controlling ultrafiltration rate of a regenerative dialysis system, comprising:
    pumping fresh dialysate fluid into a dialyzer at an input rate;
    pumping used dialysate fluid from the dialyzer at an output rate, an ultrafiltration rate of the regenerative dialysis system being related to the output rate relative to the input rate;
    filtering the used dialysate fluid to generate the fresh dialysate fluid at a sorbent cartridge;
    controlling the ultrafiltration rate of the regenerative dialysis system in response to a flow rate of the dialysate fluid through the sorbent cartridge, and in response to a corrected dialysate fluid weight;
    storing the fresh dialysate fluid at a reservoir;
    monitoring the scale weight of the fresh dialysate fluid stored in the reservoir;
    further controlling the ultrafiltration rate in response to the scale weight of the fresh dialysate fluid in the reservoir;
    calculating a dynamic weight of dialysate fluid stored in the sorbent cartridge in response to the flow rate of the dialysate fluid through the sorbent cartridge;
    calculating the corrected dialysate fluid weight by summing the dynamic weight and the scale weight;
    calculating an absorption weight of dialysate fluid stored in the sorbent cartridge as a result of time-based absorption; and
    calculating the corrected dialysate fluid rate by further summing the absorption weight with the dynamic weight and the scale weight.

* * * * *